(12) United States Patent
Runyon et al.

(10) Patent No.: US 9,150,582 B2
(45) Date of Patent: Oct. 6, 2015

(54) COMPOSITION AND METHOD FOR NEUROPEPTIDE S RECEPTOR (NPSR) ANTAGONISTS

(71) Applicant: RESEARCH TRIANGLE INSTITUTE, Research Triangle Park, NC (US)

(72) Inventors: Scott Runyon, Hillsborough, NC (US); Yanan Zhang, Apex, NC (US); Carla Hassler, Durham, NC (US); Brian Gilmour, Mebane, NC (US)

(73) Assignee: RESEARCH TRIANGLE INSTITUTE, Research Triangle Park, NC (US)

( * ) Notice: Subject to any disclaimer, the term of this patent is extended or adjusted under 35 U.S.C. 154(b) by 0 days.

(21) Appl. No.: 14/363,079

(22) PCT Filed: Dec. 6, 2012

(86) PCT No.: PCT/US2012/068257
§ 371 (c)(1),
(2) Date: Jun. 5, 2014

(87) PCT Pub. No.: WO2013/086200
PCT Pub. Date: Jun. 13, 2013

(65) Prior Publication Data
US 2015/0057268 A1    Feb. 26, 2015

Related U.S. Application Data

(60) Provisional application No. 61/568,540, filed on Dec. 8, 2011.

(51) Int. Cl.
| | | |
|---|---|---|
| C07D 491/04 | (2006.01) | |
| A61K 31/4355 | (2006.01) | |
| C07D 491/048 | (2006.01) | |
| C07D 491/10 | (2006.01) | |
| C07D 491/107 | (2006.01) | |

(52) U.S. Cl.
CPC .......... *C07D 491/048* (2013.01); *C07D 491/04* (2013.01); *C07D 491/10* (2013.01); *C07D 491/107* (2013.01)

(58) Field of Classification Search
None
See application file for complete search history.

(56) References Cited

U.S. PATENT DOCUMENTS

| | | |
|---|---|---|
| 2004/0110920 A1 | 6/2004 | Sato et al. |
| 2011/0212941 A1 | 9/2011 | Manley et al. |
| 2011/0212946 A1 | 9/2011 | Barrow et al. |

FOREIGN PATENT DOCUMENTS

| | | |
|---|---|---|
| WO | 0231145 A1 | 4/2002 |
| WO | 02055491 A2 | 7/2002 |
| WO | 2005110018 A2 | 11/2005 |

OTHER PUBLICATIONS

Gottlieb, D., et al., "Genome-wide association of sleep and circadian phenotypes", "BMC Medical Genetics", Sep. 19, 2007, pp. 1-8, vol. 8 (Suppl 1), S9.

Meis, S., et al., "Identification of a neuropeptide S responsive circuitry shaping amygdala activity via the endopiriform nucleus", "PLoS One", Jul. 16, 2008, pp. e2695 (1-11), vol. 3, No. 7.

Okamura, N., et al., "Synthesis and pharmacological in vitro and in vivo profile of 3-oxo-1,1-diphenyl-tetrahydro-oxazolo[3,4-a]pyrazine-7-carboxylic acid 4-fluoro-benzylamide (SHA 68), a selective antagonist of the neuropeptide S receptor", "The Journal of Pharmacology and Experimental Therapeutics", Mar. 12, 2008, pp. 893-901, vol. 325, No. 3.

Reinscheid, R., et al., "Pharmacological characterization of human and murine neuropeptide s receptor variants", "The Journal of Pharmacology and Experimental Therapeutics", Sep. 6, 2005, pp. 1338-1345, vol. 315, No. 3.

Rizzi, A., et al, "Neuropeptide S is a stimulatory anxiolytic agent: a behavioural study in mice", "British Journal of Pharmacology", Mar. 31, 2008, pp. 471-479, vol. 154, No. 2.

Xu, Y., et al., "Neuropeptide S: a neuropeptide promoting arousal and anxiolytic-like effects", "Neuron", Aug. 19, 2004, pp. 487-497, vol. 43, No. 4.

Xue, C., et al., "Synthesis and structure-activity relationship of a novel sulfone series of TNF-alpha converting enzyme inhibitors", "Bioorganic & Medicinal Chemistry Letters", Sep. 6, 2004, pp. 4453-4459, vol. 14, No. 17.

Zhang, Y., et al., "Identifying structural features on 1,1-diphenyl-hexahydro-oxazolo[3,4-a]pyrazin-3-ones critical for Neuropeptide S antagonist activity", "Bioorganic & Medicinal Chemistry Letters", Jun. 12, 2008, pp. 4064-4067, vol. 18.

Epsztajn, J., et al., "Reactions of the N, N-dialkylpyridlcarboxylic amides with lithium amides. Regioselective lithiation of N, N-diisopropylpyridylcarboxylic amides, a useful method for synthesis of 2, 3-and 3, 4-distributed pyridines", "Tetrahedron Letters", 1980, pp. 4739-4742, vol. 21, No. 49.

Tewari, J., et al., "CCXV. Dyes derived from cinchomeronic acid", "J. Chem. Soc.", Jan. 1, 1929, pp. 1642-1644.

*Primary Examiner* — Zinna Northington Davis
(74) *Attorney, Agent, or Firm* — Hultquist, PLLC; Mary B. Grant

(57) ABSTRACT

Neuropeptide S receptor antagonists are provided that bind in functional assays to neuropeptide S receptors; methods are provided for use of these antagonists in treatment of conditions or disease states that are ameliorated by blocking of the neuropeptide S receptor, including substance abuse and substance abuse relapse; and for use of neuropeptide S receptor antagonists in the manufacture of therapeutics and pro-drugs for therapeutics useful in disease states and conditions sensitive to binding of the neuropeptide S receptor.

15 Claims, 3 Drawing Sheets

Reagents and conditions comprise: 1) LDA, Et$_2$O, -78° C, 4-fluorophenyl isovalerophenone; b) 6 N HCl; c) H$_2$ (40 psi), PtO$_2$, EtOH, HCl.

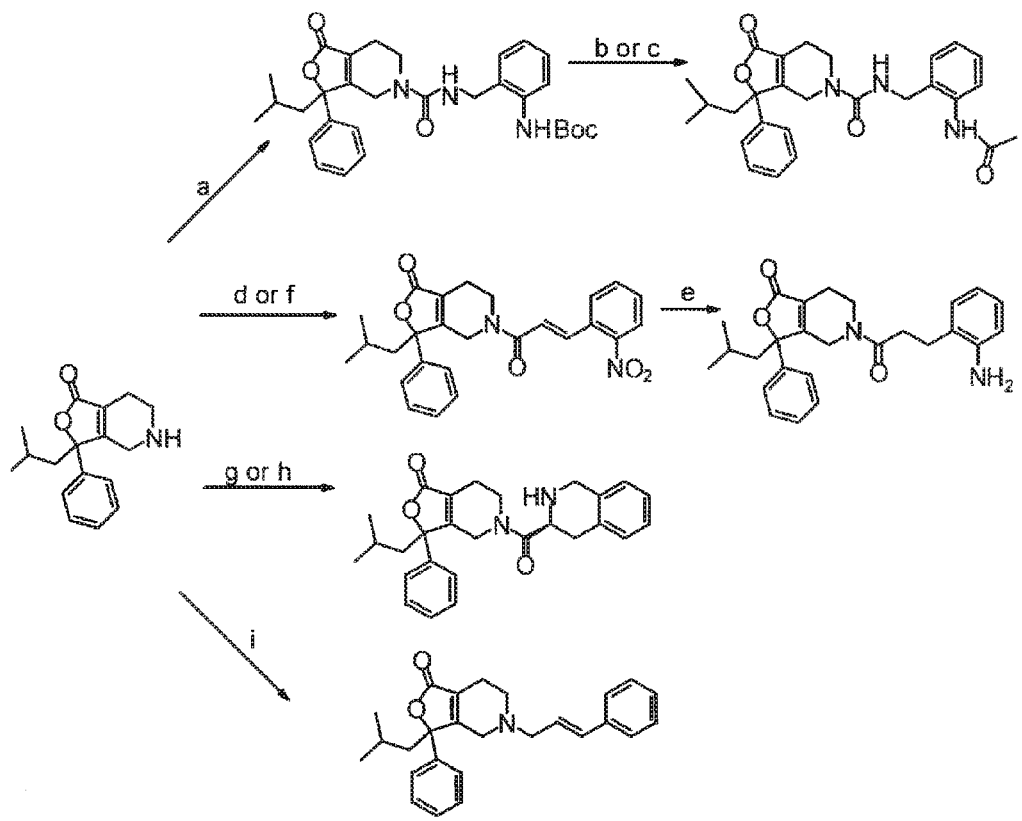

*Reagents and conditions:* a) triphosgene, NEt₃, *tert*-butyl 2-(aminomethyl)-phenylcarbamate, THF, 0 °C to rt; b) 1. TFA, CH₂Cl₂; 2. NEt₃, acetyl chloride, CH₂Cl₂; c) 1. TFA, CH₂Cl₂; 2. BOP, *N,N'*-diisopropylethylamine, acetic acid, CH₂Cl₂; d) BOP, *N,N'*-diisopropylethylamine, *E*-3-(2-nitrophenyl)acrylic acid, CH₂Cl₂; e) H₂ (1 atm), 10% Pd/C, EtOH/EtOAc; f) NEt₃, *E*-3-(2-nitrophenyl)acryloyl chloride, THF; g) 1. BOP, *N,N'*-diisopropylethylamine, (*S*)-2-(((9H-fluoren-9-yl)methoxy)carbonyl)-1,2,3,4-tetrahydroisoquinoline-3-carboxylic acid; 2. piperidine, DMF; h) 1. BOP, *N,N'*-diisopropylethylamine, (*S*)-2-(*tert*-butoxycarbonyl)-1,2,3,4-tetrahydroisoquinoline-3-carboxylic acid; 2. TFA, CH₂Cl₂; i) *trans*-cinnamaldehyde, NaHB(OAc)₃, THF.

FIG. 2

ID NO: 1). This sequence is also well conserved among species; in particular, the serine (S)N-terminal residue of NPS is conserved among all species examined so far. After its pairing with NPS, the previously orphan G-protein coupled receptor (GPCR) GPR154 was named the NPS receptor and abbreviated as NPSR.

SEQUENCE LISTING

```
<160> NUMBER OF SEQ ID NOS: 1

<210> SEQ ID NO 1
<211> LENGTH: 20
<212> TYPE: PRT
<213> ORGANISM: Human

<400> SEQUENCE: 1

Ser Phe Arg Asn Gly Val Gly Thr Gly Met Lys Lys Thr Ser Phe Gln
1               5                   10                  15

Arg Ala Lys Ser
            20
```

COMPOSITION AND METHOD FOR NEUROPEPTIDE S RECEPTOR (NPSR) ANTAGONISTS

GOVERNMENT LICENSE RIGHTS

This invention was made with government support under Grants Nos. 1R21MH081247-01 and 1R01MH087826-01A1 awarded by the National Institute of Health. The government has certain rights in this invention.

CROSS-REFERENCE TO RELATED APPLICATIONS

This application is a U.S. national phase under the provisions of 35 U.S.C. §371 of International Patent Application No. PCT/US12/68257 filed Dec. 6, 2012, which in turn claims priority of U.S. Provisional Patent Application No. 61/568,540 filed Dec. 8, 2011. The disclosures of such international patent application and U.S. priority provisional patent application are hereby incorporated herein by reference in their respective entireties, for all purposes.

FIELD

The subject matter disclosed herein relates to Neuropeptide-S receptor ligands and more particularly relates to Neuropeptide-S Receptor antagonists for the treatment of a disease or condition responsive to blocking of the Neuropeptide-S Receptor.

BACKGROUND

Human Neuropeptide S (NPS) is a 20 residue peptide showing the primary sequence: SFRNGVGTGMKKTS-FQRAKS (SEQ ID NO: 1). This sequence is also well conserved among species; in particular, the serine (S)N-terminal residue of NPS is conserved among all species examined so far. After its pairing with NPS, the previously orphan G-protein coupled receptor (GPCR) GPR154 was named the NPS receptor and abbreviated as NPSR.

NPS peptide transcript is expressed predominantly in a small group of neurons located between the locus ceruleus (LC), the Barrington nucleus, and the parabrachial nuclei. NPSR mRNA is expressed throughout the central nervous system with the highest concentration in olfactory structures, the amygdaloid complex, the paraventricular thalamic nucleus, the subiculum, and the lateral (LH), dorsomedial (DMH), and ventromedial hypothalamus (VMH). NPSR shows potential for involvement in several biological processes such as arousal, anxiety, and food intake.

SUMMARY

Provided herein is a Neuropeptide-S Receptor (NPSR) antagonist configured to bind to NPSR with high affinity. In some embodiments the NPSR antagonist provided may serve as an intermediate for the synthesis of biologically active compounds. In certain embodiments the NPSR antagonist is in the form of a pharmaceutically acceptable salt.

Further provided is a pharmaceutical composition comprising an effective amount of a NPSR antagonist and a physiologically acceptable carrier. Also provided is a method of binding a NPSR in a subject in need thereof, comprising administering to said subject an effective amount of NPSR antagonist. In some embodiments the subject is a mammal, including but not limited to a human.

In certain embodiments the method of binding the NPSR comprises administering an effective amount of an NPSR antagonist to a subject having a disease state selected from the group consisting of opiate addiction, cocaine addiction, nicotine addiction and ethanol addiction. The compound is sometimes administered orally, intravenously, or intramuscularly.

Also provided herein is method for preventing and/or treating at least one of a disease or condition attributable to binding of an agonist to the NPSR in a mammal, which comprises administering an effective amount of an NPSR antagonist or a salt thereof to a mammal. In certain embodiments the disease or condition is substance abuse, relapse from substance abuse, panic disorder, phobia, post-traumatic stress disorder, and sleep disorder including narcolepsy.

Further provided herein is a method for use of an NPSR antagonist as disclosed herein in the manufacture of a prophylactic and/or therapeutic agent or pro-drug for at least one of a disease or condition attributable to binding of an agonist to the neuropeptide-S Receptor. In some embodiments the disease or condition is substance abuse, relapse from substance abuse, panic disorder, phobia, post-traumatic stress disorder, and sleep disorder including narcolepsy.

Also provided herein is a method of synthesis for alternatively substituted 4,5,6,7-tetrahydrofuro[3,4-c]pyridin-1 (3H)-ones and alternately substituted (trans and cis 3a,7a)-1-oxo-3,3-disubstitutedhexahydrofuro[3,4-c]pyridine-5(1H)-carboxamides.

BRIEF DESCRIPTION OF THE DRAWINGS

In order that the advantages of the embodiments of the invention will be readily understood, a more particular description of the embodiments briefly described above will be rendered by reference to specific embodiments that are illustrated in the appended drawings. Understanding that these drawings depict only some embodiments and are not therefore to be considered to be limiting of scope, the embodiments will be described and explained with additional specificity and detail through the use of the accompanying drawings, in which:

FIG. 2 illustrates a representative synthetic scheme for Compound 1 derivatives.

DETAILED DESCRIPTION

Figure 1:
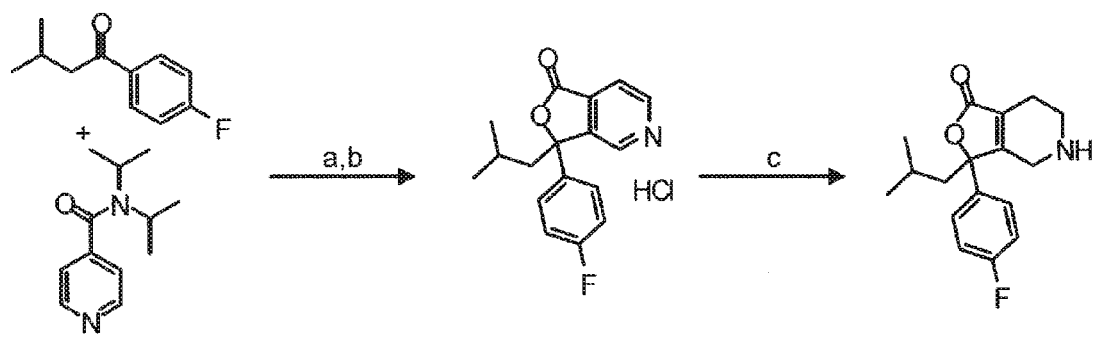
FIG. 1 illustrates a synthetic scheme for Compound 1 herein.
Figure 3:
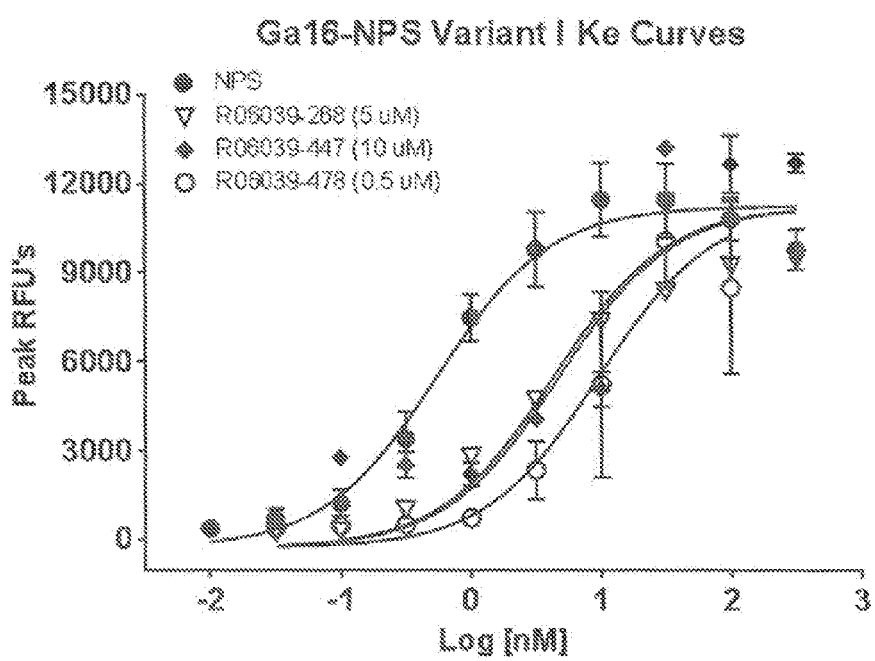
FIG. 3 illustrates antagonist activity of selected NPS antagonists where Ke represent the ability of antagonist test compounds to rightwardly shift the NPS EC50 curve.

References throughout this specification to features, advantages, or similar language do not imply that all of the features and advantages may be realized in any single embodiment. Rather, language referring to the features and advantages is understood to mean that a specific feature, advantage, or characteristic is included in at least one embodiment. Thus, discussion of the features and advantages, and similar language, throughout this specification may, but do not necessarily, refer to the same embodiment.

Furthermore, the described features, advantages, and characteristics of the embodiments may be combined in any suitable manner. One skilled in the relevant art will recognize that the embodiments may be practiced without one or more of the specific features or advantages of a particular embodiment. In other instances, additional features and advantages may be recognized in certain embodiments that may not be present in all embodiments.

These features and advantages of the embodiments will become more fully apparent from the following description and appended claims, or may be learned by the practice of embodiments as set forth hereinafter. As will be appreciated by one skilled in the art, aspects of the present invention may be embodied as a composition, method, and/or system.

Reference throughout this specification to "one embodiment," "an embodiment," or similar language means that a particular feature, structure, or characteristic described in connection with the embodiment is included in at least one embodiment. Thus, appearances of the phrases "in one embodiment," "in an embodiment," and similar language throughout this specification may, but do not necessarily, all refer to the same embodiment, but mean "one or more but not all embodiments" unless expressly specified otherwise. The terms "including," "comprising," "having," and variations thereof mean "including but not limited to" unless expressly specified otherwise. An enumerated listing of items does not imply that any or all of the items are mutually exclusive and/or mutually inclusive, unless expressly specified otherwise. The terms "a," "an," and "the" also refer to "one or more" unless expressly specified otherwise.

Furthermore, the described features, structures, or characteristics of the embodiments may be combined in any suitable manner. One skilled in the relevant art will recognize, that embodiments may be practiced without one or more of the specific details, or with other methods, components, materials, and so forth. In other instances, well-known structures, materials, or protocols are not shown or described in detail to avoid obscuring aspects of an embodiment.

Introduction

The molecules provided herein bind with high affinity to NPSR, thus excluding or displacing NPS and functioning as antagonists. The molecules provided may be useful in the treatment of cocaine addiction, substance abuse, relapse from substance abuse, panic disorder, phobia, post-traumatic stress disorder, and sleep disorder including narcolepsy other conditions.

Receptor Antagonists

A receptor antagonist is a type of receptor ligand or drug that does not provoke a biological response itself upon binding to a receptor, but blocks or dampens natural ligand, or agonist, mediated responses. In pharmacology, antagonists have affinity but no efficacy for their cognate receptors, and binding will disrupt the interaction and inhibit the function of an agonist or inverse agonist at receptors. Antagonists mediate their effects by binding to the active site or to allosteric sites on receptors, or they may interact at unique binding sites not normally involved in the biological regulation of the receptor's activity. Antagonist activity may be reversible or irreversible depending on the longevity of the antagonist-receptor complex, which, in turn, depends on the nature of antagonist receptor binding. Drug antagonists may achieve their potency by competing with endogenous ligands or substrates at structurally-defined binding sites on receptors.

Neuropeptide S and Neuropeptide S Receptor

In neurological science the coupling of putative transmitter molecules with "orphan" receptors of unknown function has led to the identification of several interesting ligand-receptor pairings that exhibit novel pharmacology. The neuropeptide S receptor (NPSR) system was deorphanized by Sato and co-workers (1) by demonstrating pairing with NPS and has been shown to modulate a variety of physiological states such as sleep, feeding, anxiety, drug abuse, and inflammation.

Neuropeptide S is a 20-amino acid peptide that functions as an agonist through activation of its cognate $G_q$ or $G_s$ coupled, GPCR receptor system. The NPSR has at least three known isoforms, the wild type HPSAsn$^{107}$, the SNP Asn$^{107}$ Ile, and NPS C-Alt. Since each variant could potentially have functions differences, the agonist sensitivity of each isoform was evaluated. Radioligand binding of [$^{125}$I]Tyr$^{10}$-NPS was unaltered among receptor variants. However, a five to ten fold enhancement in functional sensitivity using calcium flux was observed for the Ile$^{107}$ variant over Asn$^{107}$. In a functional assay, hNPS was the least potent at NPSR-C0Alt (30 fold lower versus the 107I variant).

The activation of NPSR by NPS results in elevated intracellular calcium via the NPSR cognate proteins. Amino acids important for NPS agonist activity have been identified through Ala scanning mutagenesis. In particular, Phe 2, Arg 3, Asn 4, and Val 6 are critical for agonist activity, whereas residues 5-13 are hypothesized to form an α-helical recognition sequence. NMR and circular dichroism studies on NPS have indicated a significant degree of flexibility among the amino acids critical for receptor activation, thus making identification of the bioactive NPS conformer difficult using currently available data.

Xu and colleagues (2) determined that NPS was involved in both arousal and anxiety. Administration of NPS (i.c.v.) increased locomotor activity in both habituated and naive mice. NPS-treated mice also demonstrated anxiolytic-like behaviors in the elevated plus maze, light dark box, and marble burying paradigm. In more recent studies, Rizzi and co-workers (3) confirmed the arousal and anxiolytic promoting properties of NPS using stress-induced hypothermia, which is a behavioral model insensitive to alterations in locomotor activity.

Anxiolytic

Defining both receptor and peptide localization in the central nervous system (CNS) provided the first indication of NPS function. In situ hybridization showed NPSR mRNA was expressed widely throughout the CNS. In particular, high levels of NPSR mRNA were identified in the thalamus, hypothalamus, cortex, hippocampus, and amygdala. Human NPS precursor mRNA, however, is largely expressed in the locus ceruleus (LC) of the brainstem and is cleaved from an 89 amino acid signal peptide at a specific cleavage site adjacent to the amino acids Arg Lys. Due to mRNA localization in the LC, Xu and colleagues hypothesized that NPS may play a role in arousal, anxiety, or both.

It is often difficult to assess anxiolytic activity for drugs that increase locomotor stimulation because the associated behavioral assays generally employ an exploratory or locomotor component. Since NPS was postulated to modulate two physiological states that can be difficult to distinguish in standard behavioral analysis, Xu and colleagues measured arousal and anxiolytic activity in manners independent from each other.

Mice have a tendency to show increased locomotor activity when introduced into a novel environment. Administration of NPS (i.c.v.) caused on increase in locomotor activity of habituated mice versus naïve mice suggesting arousal independent of anxiolysis. NPS-treated mice also demonstrated anxiolytic-like behaviors in the elevated plus maze, light dark box, and marble burying paradigms. In more recent studies, Rizzi and co-workers (3) confirmed the arousal and anxiolytic promoting properties of NPS using stress induced hypothermia, which is a behavioral model insensitive to alterations in locomotor activity.

Preliminary studies in vivo now demonstrate the very unique pharmacological profile for NPS indicating a promising role for NPS and NPSR as viable therapeutic targets. Molecules provided herein may modulate anxiety and may be useful in the treatment of conditions including panic disorders, phobias, and post-traumatic stress disorder.

NPS Modulates Sleep

Ongoing research with the NPS receptor system has begun to identify a number of potential disease states such as narcolepsy, panic disorders, obesity, drug abuse, post-traumatic stress disorder, and anxiety that may be responsive to NPS-related pharmacotherapies. The development of new drugs acting through the NPS receptor system may significantly benefit individuals intolerant of, or unresponsive to currently employed therapies. The NPS receptor system has shown promise as a target for non-sedating anxiolytics. Administration of NPS (i.c.v.) increased wakefulness while simultaneously reducing anxiety in rodents, yet NPS mediated arousal is not controlled by noradrenergic neurons.

Double in situ hybridization experiments have indicated that NPS expressing neurons in the LC do not express norepinephrine, but are primarily glutamatergic. Identification of NPS has also led to the discovery of a previously undefined population of cells. NPS expressing neurons have now been identified in an area between Barrington's nucleus and the LC proper. These cells do not express either norepinephrine or corticotrophin-releasing factor although they do express NPS. Further study of these NPS expressing cells may provide definitive proof of a previously hypothesized role of the pons in arousal and sleep.

The Sleep Heart Study (4) provided additional genetic data for the role of NPS in sleep. Participants were questioned about their sleep duration, daytime sleepiness and quality of sleep. The participants were then genotyped to identify potential genetic associations with beneficial sleep habits. A specific association between usual bedtime and the NPS N107I SNP was discovered. This study concluded the NPS was a likely mediator of sleep.

The ability of NPS to alter the sleep-wake patterns of mice was also evaluated using electroencephalograms and electromylograms. Low dose NPS (0.1 nMol) in mice increased the first hour of wakefulness from 45% to 69% compared to saline. Moreover, the amount of stage 1 and 2 slow wave sleep and REM sleep were significantly reduced compared to saline.

This level of NPS involvement in modulating sleep demonstrates the NPS pharmacotherapies may benefit patients suffering from insomnia or narcolepsy. Molecules provided herein may modulate sleep by and may be useful in the treatment of sleep disorders including insomnia and narcolepsy.

NPS Alters the Rewarding Effects of Cocaine

NPS receptors in the amygdala localize in areas previously shown to be involved in drug abuse and addiction. In addition, NPS is co-localized with corticotrophin releasing-factor (CRF) in the lateral parabrachial nucleus. The co-localization of NPS with CRF is of interest because NPS decreases anxiety whereas CRF increases anxiety. CRF has been shown to modulate drug abuse behaviors.

In order to better define a potential role for NPS in drug-abuse, previous studies have evaluated the ability of NPS to reinstate previously extinguished cocaine seeking behaviors and have found that NPS administered i.c.v dose-dependently increased formerly extinguished cocaine seeking behaviors in mice. The inventors herein have determined that NPS antagonists reduce cocaine self-administration in rats. Molecules provided herein may be useful in the treatment of drug addiction including substance abuse and relapse from substance abuse.

NPS Alters Learning and Memory

NPSR mRNA is expressed at very high levels in hippocampal areas known for regulating learning and memory including the endopiriform cortex/nucleus and the subiculum. Therefore, NPS is positioned to be involved in memory and the consolidation of memory. NPS administration (i.c.v.) dose-dependently improves performance in novel recognition assays, confirming a biochemical role in memory. Since NPS modulates both memory and anxiety, the ability of NPS to alter the transformation from short-term memory to long-term memory (consolidation) has been investigated due in part to the potential implications for treating memory-associated anxiety disorders.

Anxiety disorders are represented among a significant proportion of the population and current pharmacotherapies such as Benzodiazephines carry unwanted side-effects such as sedation and potential dependence. The choice of an appropriate biological target for anxiety related disorders should consider both the biochemical mechanisms leading to the acquisition of fear, but more importantly, the ability to eliminate its persistence. A study by Reinsheid and colleagues (5) has begun to identify a role for NPS in the induction of acute anxiolytic-like effects in addition to the simultaneous reduction in the consolidation of aversive memories. Mice subjected to Pavlovian fear conditioning were administered NPS prior to testing.

NPS administration pre-testing decreased the fear response (freezing behavior), whereas NPS administration pre-training had no effect on fear response. This indicated that NPS was involved in mitigating fear expression as opposed to inhibiting fear learning. This study demonstrated that activation of the NPS receptor possessed a dual role in mitigating anxiety. In addition to the acute effects NPS has on anxiety (elevated plus maze, light dark box, marble burying), the more important role of facilitating extinction of aversive memories was now identified. This demonstrates that targeting the NPSR with small molecule agonists may have the potential to effectively treat anxiety and anxiety related disorders such as post-traumatic stress disorder (PTSD).

Other studies have elucidated the role of NPS in learning and memory (Meis and colleagues (6)). In order to clarify selective alteration of contextual fear memory retrieval versus cued fear memory retrieval, NPS was injected into the basolateral amygdala (BLA) and a percentage of freezing behaviors evaluated. NPS injections (0.1 nM) significantly reduced contextual fear memories when the animals were placed in the aversive environment following training, but not the Pavlovian cue induced fear memories when a tone preceded an upcoming footshock. No anxiolytic activity was observed at this low dose of NPS suggesting that enhanced locomotion or anxiolytic action was not responsible for the reduction in contextual freezing events.

The ability to block the conversion of contextual fear to long-term memories but not cue induced memories indicates a specific role for NPS pharmacotherapies in memory consolidation. Molecules provided herein may be useful in treatment of contextually induced anxiety including various phobias.

NPSR Antagonist Molecules

Herein provided are NPSR antagonists useful as small molecule probes for the pharmacological characterization of NPS receptors and as therapeutics for NPSR modulated conditions. Antagonist molecules as provided herein may be used to alleviate conditions caused or aggravated by the binding of NPS to the NPSR receptor. In some embodiments an NPSR antagonist as provided herein has a binding activity of Ke less than 200 nM. In certain embodiments an NPSR antagonist has a binding activity of Ke less than 100 nM.

It is understood that the structures provided herein include all stereoisomers, plus and minus isomers, diastereoisomers, enantiomers of the diastereoisomers, and conformers of the molecules provided. In embodiments, a neuropeptide S receptor antagonist is provided comprising a compound of structure (I):

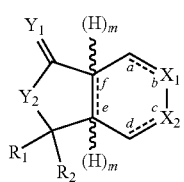

(I)

where the dotted lines denote a saturated or unsaturated bond, with the proviso that either all dotted lines denote an unsaturated bond, only the dotted line between e and f is an unsaturated bond or none of the dotted lines denote an unsaturated bond; $X_1$ is CH, $CH_2$, N or N—$R_3$ and $X_2$ is CH when $X_1$ is N, $X_2$ is $CH_2$ when $X_1$ is N—$R_3$, $X_2$ is N when $X_1$ is CH, and $X_2$ is N—$R_3$ when $X_1$ is $CH_2$; m is 0 or 1; and the wavy lines represent bonds connected to carbons having cis- or trans-configuration. $Y_1$ is O or S and $Y_2$ is O, N or $CH_2$. The substituents for $R_1$, $R_2$ and $R_3$ are described below.

In some embodiments the NPSR antagonists provided herein are selected from the group consisting of structural formulas (1), (2), (3), (4) and (5). In formula (1), $X_1$ is one of CH and N and $X_2$ is the other of CH and N. In formulas (2), (3), (4), and (5), $X_1$ is one of $CH_2$ and N—$R_3$ and $X_2$ is the other of $CH_2$ and N—$R_3$.

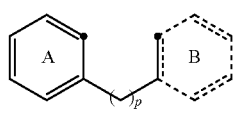

(1)

(2)

(3)

(4)

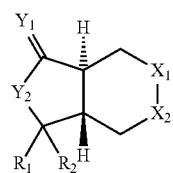

(5)

where $Y_1$ is O, or S and $Y_2$ is O, N, or $CH_2$.

In embodiments, $R_1$ and $R_2$ are jointly structure (II):

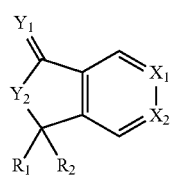

(II)

where p is 0 or 2 if ring B is present and p is 2 if ring B is not present. In an alternative representation, $R_1$ and $R_2$ are jointly one of the following structures (bonding carbons shown in bold):

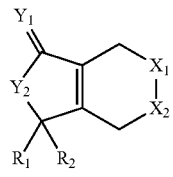

(1a)

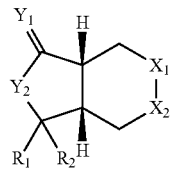

(1b)

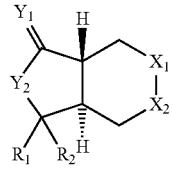

(1c)

or $R_1$ and $R_2$ may also each be independently, methyl alcohol, phenyl, straight chain or branched $C_{1-8}$ alkyl, $C_{3-6}$ cycloalkyl, $C_{2-8}$ alkenyl, $C_{2-8}$ alkynyl, $C_{6-10}$ aryl or heterocycle, substituted aryl, thiophene, or furan.

In some embodiments $R_1$ and $R_2$ are each independently aryl having halogens at position 3 and 4 independently, aryl having alkoxy, methoxy, ethoxy, benzyloxy, hydroxyl at positions 2 and 3 independently, aryl having trifluoromethyl at position 4, or one of the following structures:

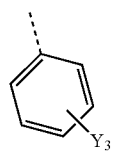

(1d)

where $Y_3$ may be at any position on the ring and comprises H, halogen, OH, $C_{1-4}$alkyl, $C_{1-4}$hydroxyalkyl, or $CF_3$.

In various embodiments, $R_1$ and $R_2$ are independently one of the following structures;
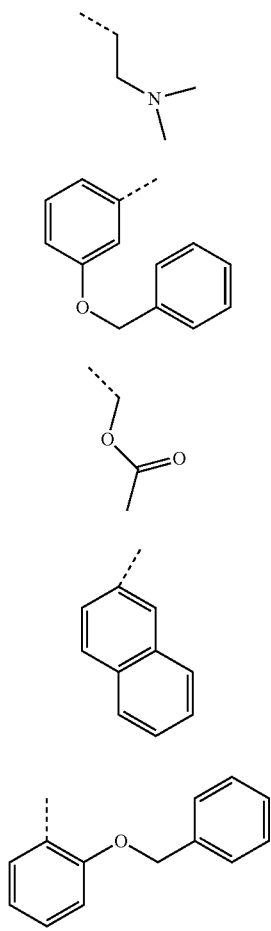
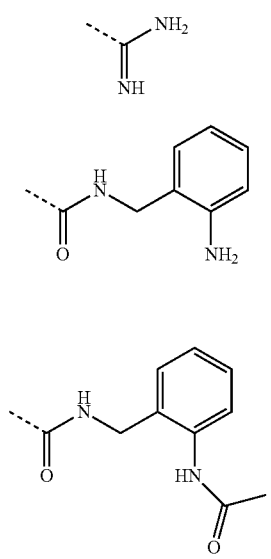
$R_3$ is one of the following structures:
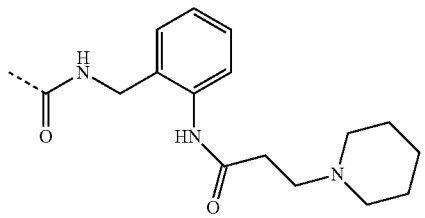
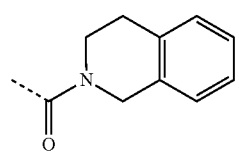
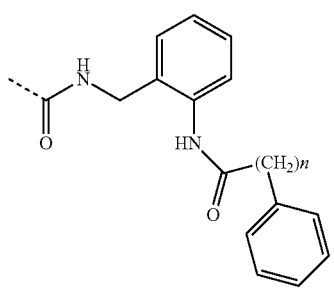
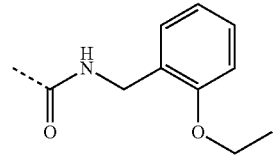
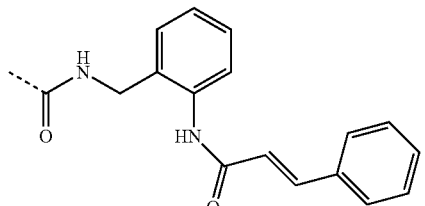
where n = 0 to 3
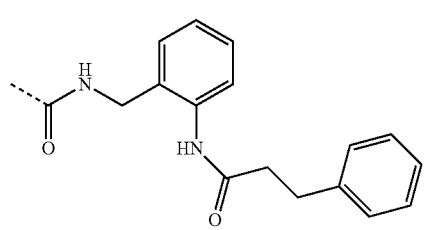
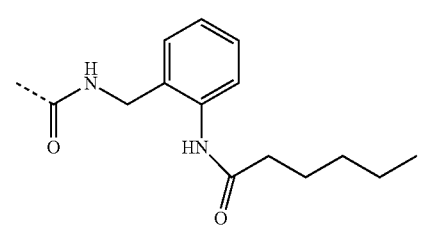

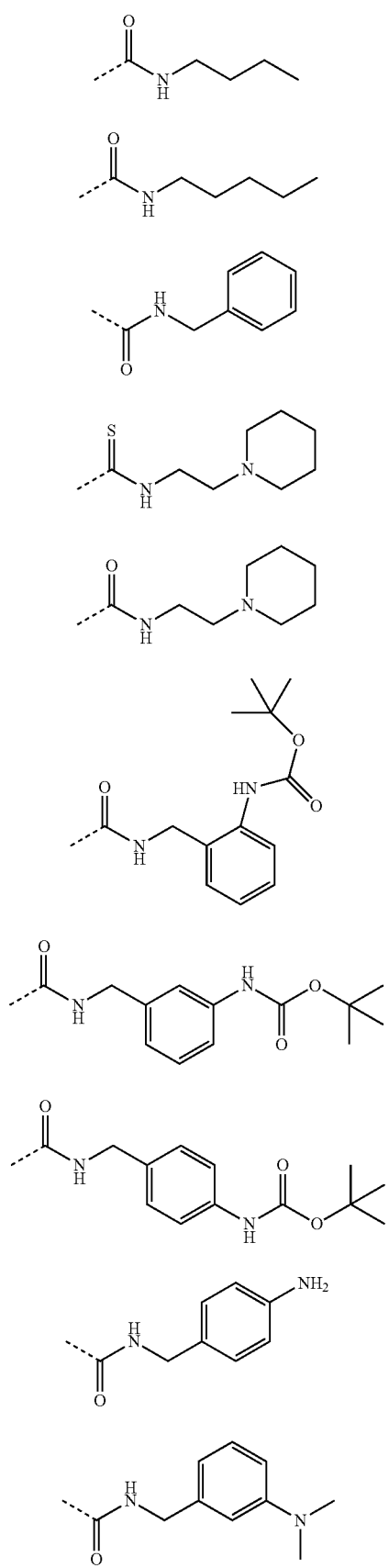
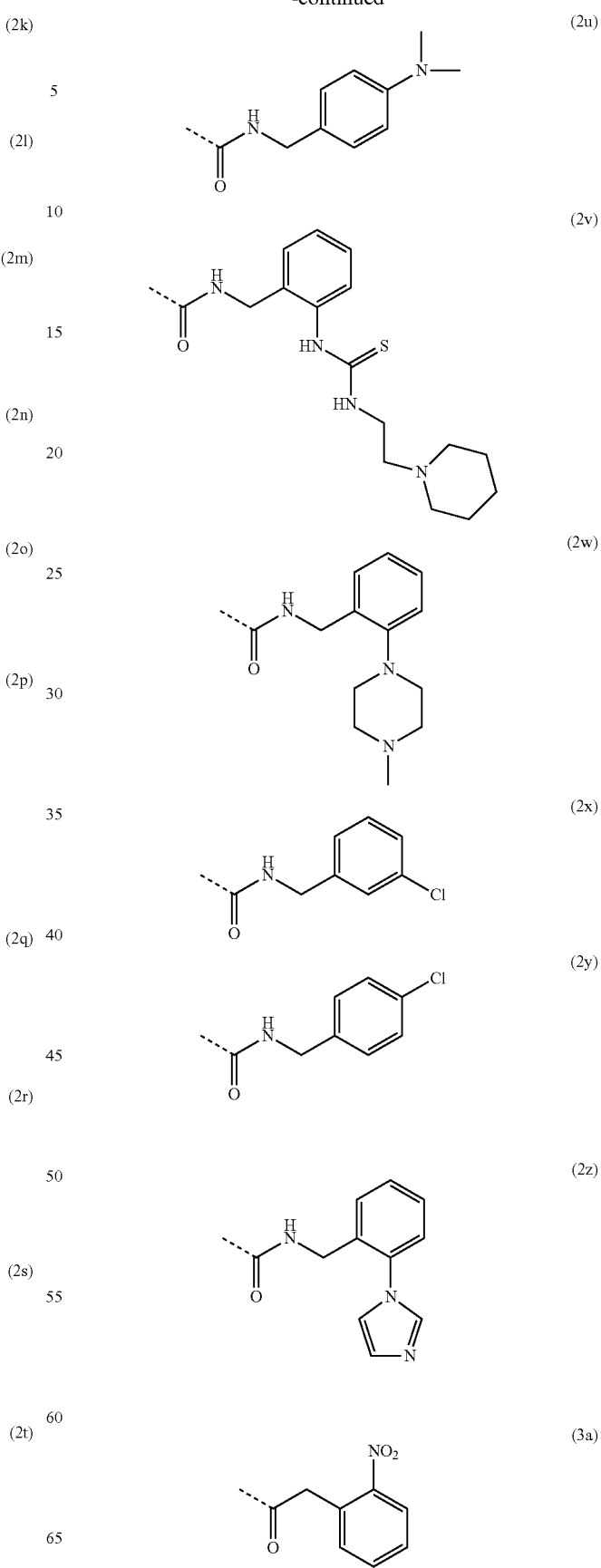

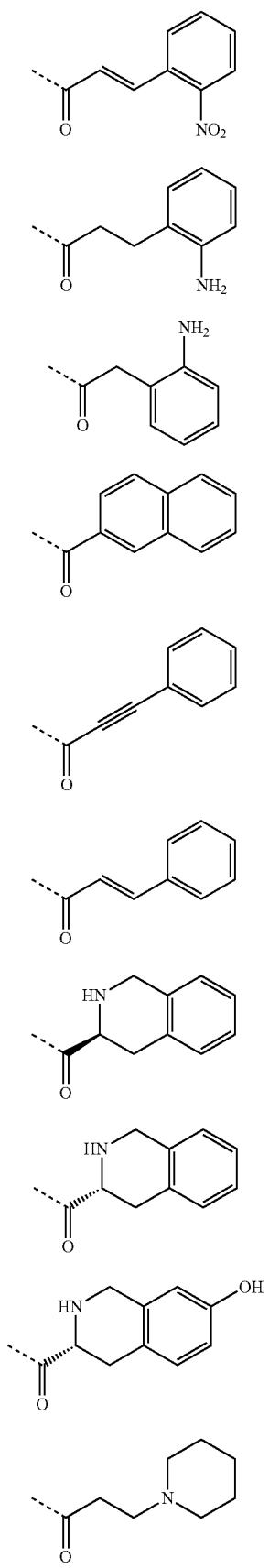
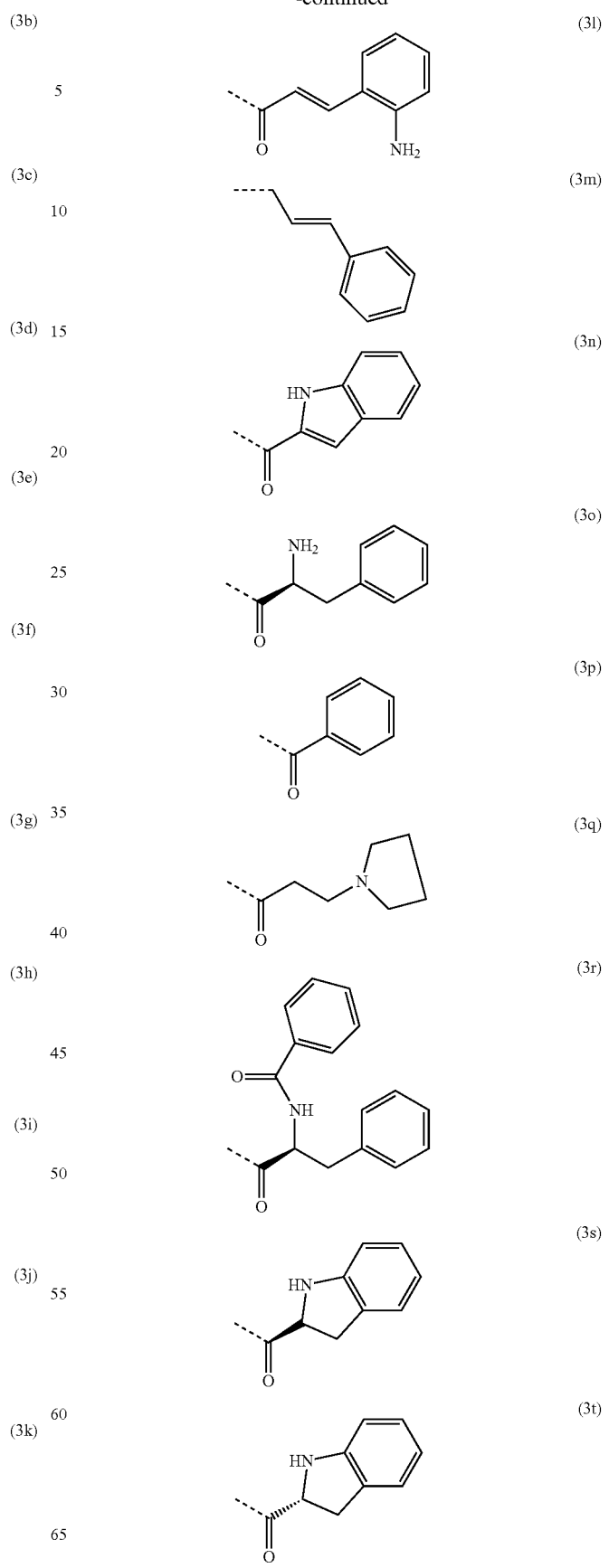

-continued

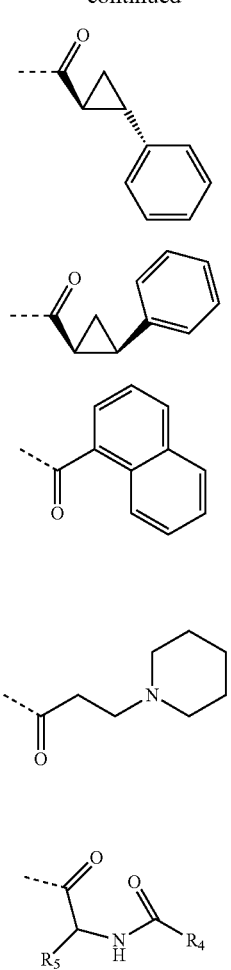

(3u)

(3v)

(3w)

(3x)

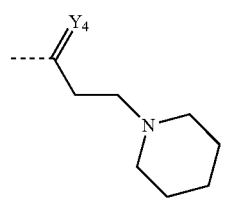

(3y)

where $R_5$ is $C_{1-8}$ alkyl, $C_{3-6}$ cycloalkyl, $C_{2-8}$ alkenyl, $C_{2-8}$ alkynyl, $C_{6-10}$ aryl, heterocycle, substituted aryl, substituted thiophene, furan, pyrrole, a natural amino acid side chain, or an unnatural amino acid side chain selected from the group consisting of Norleucine, Cyclohexylalanine, Homocyclohexylalanine, Cyclohexylglycine, 2-amino isobutyric acid, 3-Cyclopentylalanine, Norvaline, and homophenylalanine; and $R_4$ is $C_{1-8}$ alkyl, $C_{3-6}$ cycloalkyl, $C_{2-8}$ alkenyl, $C_{2-8}$ alkynyl, $C_{6-10}$ aryl, heterocycle, substituted aryl, substituted thiophene, furan, pyrrole, or H; or (3z)

where $Y_4$ may be O or S.

In embodiments, the substituents for $R_3$ may be represented as —C(=NH)NH$_2$, —CONH(CH$_2$)$_3$CH$_3$, —CONH(CH$_2$)$_4$CH$_3$,

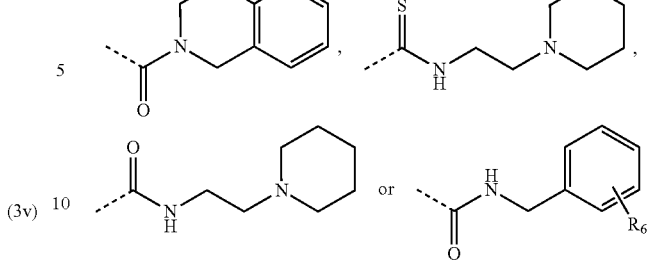

where $R_6$ may be at any position on the ring and is H, NH$_2$, NHCOCH$_3$, —OCH$_2$CH$_3$, NHCO(CH$_2$)$_4$CH$_3$, N(CH$_3$)$_2$, NHCOOC(CH$_3$)$_3$, halogen, NHCOCH$_2$CH$_2$N⟨piperidine⟩, —NHCO(CH$_2$)$_n$—⟨phenyl⟩, wherein n is 0 to 3;

—NHCOCH=CH—⟨phenyl⟩, —N⟨piperazine⟩N—CH$_3$,

—N⟨imidazole⟩N, NHCSNHCH$_2$CH$_2$—⟨piperidine⟩;

or one of the structures labeled (3a) to (3z) above. In embodiments, the substituent for $R_6$ may be in the ortho or para position on the ring.

As used throughout this disclosure, the terms "alkyl group" or "alkyl radical" encompass all structural isomers thereof, such as linear, branched and cyclic alkyl groups and moieties. Unless stated otherwise, all alkyl groups described herein may have 1 to 8 carbon atoms, inclusive of all specific values and subranges therebetween, such as 2, 3, 4, 5, 6, or 7 carbon atoms.

The alkenyl group or alkynyl group may have one or more double or triple bonds, respectively. As will be readily appreciated, when an alkenyl or alkynyl group is bonded to a heteroatom a double or triple bond is not formed with the carbon atom bonded directly to the heteroatom.

The aryl group is a hydrocarbon aryl group, such as a phenyl, naphthyl, phenanthryl, anthracenyl group, which may have one or more $C_{1-4}$ alkyl group substituents.

The compounds referred to as structural formulas (1) and (2) can be synthesized according to the general reaction sequence described in FIG. 1. Deprotonation of 4-diisopropylamidopyridine with a suitable base having an appropriate pKa of greater than 30 such as lithium diisopropylamide in diethylether will afford an anion that is then condensed with an appropriately substituted ketone such as of 1-(4-fluorophenyl)-3-methylbutan-1-one to provide an appropriately substituted intermediate such as 3-[1-(4-fluorophenyl)-1-hydroxy-3-methylbutyl]-N,N-diisopropylpyridine-4-carboxamide. The intermediate is then treated with and acid to induce cyclization providing substituted compounds such as 3-(4-fluorophenyl)-3-isobutylfuro[3,4-c]pyridin-1(3H)-one. The resulting [3,4-c]pyridin-1(3H)-one and analogous compounds can be reduced by treatment with an equivalent of acid, a metal such as platinum oxide, and hydrogen under a pressure between 10 and 40 psi to provide compounds seen in structural formula (2).

In particular compounds referred to as structural formula (3), are obtained by further reduction of the appropriately substituted 4,5,6,7-tetrahydrofuro[3,4-c]pyridin-1(3H)-one with nickel boride to afford the cis configuration as demonstrated for compounds referred to in structural formula (3) including R06039-211. Epimerization of the cis configuration at the 3,7 positions to the trans configuration at the 3,7 positions can be accomplished through the use of a base such as sodium methoxide in an aprotic or protic solvent to provide compounds referred to in structural formulas (4) and (5) including R060039-212. Condensation of appropriately substituted carboxylic acids with structural formulas (2)-(5) where $R_3$=H using a coupling reagent such as BOP and a non-nucleophilic base such as triethylamine, affords the target compounds represented by structural formulas (2b)-(3l).

The compounds referred to as structural formulas (1)-(5) with N and N—$R_3$ in the X position can be synthesized in a manner analogous to that described for structural formulas (1)-(5) with the exception that the synthesis employs 3-diisopropylamidopyridine instead of 4-diisopropylamidopyridine as the starting material. All other reaction conditions are analogous.

Compound (2a) is prepared by treating 3-phenyl-3-isobutyl-4,5,6,7-tetrahydrofuro[3,4-c]pyridin-1(3H)-one with 1,3-bis-tert-butoxycarbonyl-2-methyl-2-thiopseudourea and mercury chloride in DMF and triethylamine at 50° C. for 20 hours.

As provided herein, alternately substituted analogs of 4,5, 6,7-tetrahydrofuro[3,4-c]pyridin-1(3H)-ones are prepared using platinum oxide, hydrogen, and one equivalent of strong acid. This reduction has been optimized to afford only the tetrahydro derivatives and not the fully reduced analogs. Further provided is a high yielding method using nickel boride for the reduction and alkoxide bases for the epimerization which in some embodiments is used to prepare alternatively substituted 4,5,6,7-tetrahydrofuro[3,4-c]pyridin-1(3H)-ones and alternately substituted (trans and cis 3a,7a)-1-oxo-3,3-disubstitutedhexahydrofuro[3,4-c]pyridine-5 (1H)-carboxamides.

Formulation and Administration

Those compounds provided herein may be in the form of a pharmaceutically acceptable salt via protonation of the amines with a suitable acid. Suitable acids known to those of ordinary skill in the art include, for non-limiting example, hydrochloric, hydriodic, hydrobromic, sulfuric, phosphoric, citric, acetic, fumaric, tartaric, and formic acids.

The salts of compounds provided herein and intermediates thereof may be exemplified by metal salts, ammonium salts, salts with organic bases, salts with inorganic acids, salts with organic acids, salts with basic or acidic amino acids, or the like. Suitable examples of the metal salt include alkali metal salts such as sodium salts and potassium salts; alkaline earth metal salts such as calcium salts, magnesium salts and barium salts; aluminum salts; and the like. Suitable examples of the salt with an organic base include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like.

Suitable examples of the salt with an inorganic acid include salts with hydrochloric acid, hydrobromic acid, nitric acid, sulfuric acid, phosphoric acid and the like. Suitable examples of the salt with an organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like. Suitable examples of the salt with a basic amino acid include salts with arginine, lysine, ornithine and the like, and suitable examples of the salt with an acidic amino acid include salts with aspartic acid, glutamic acid and the like.

Salts may be pharmaceutically acceptable. For example, when the compound has an acidic functional group, mention may be made of inorganic salts such as alkali metal salts (e.g., sodium salts, potassium salts, etc.), alkaline earth metal salts (e.g., calcium salts, magnesium salts, barium salts, etc.) and the like, ammonium salts, and the like; when the compound has a basic functional group, mention may be made of salts with inorganic acids such as hydrobromic acid, nitric acid, sulfuric acid, phosphoric acid and the like, or salts with organic acids such as acetic acid, phthalic acid, fumaric acid, oxalic acid, tartaric acid, maleic acid, citric acid, succinic acid, methanesulfonic acid, p-toluenesulfonic acid and the like.

When the compound has an acidic functional group, mention may be made of inorganic salts such as alkali metal salts (e.g., sodium salts, potassium salts, etc.), alkaline earth metal salts (e.g., calcium salts, magnesium salts, barium salts, etc.) and the like, ammonium salts, and the like; when the compound has a basic functional group, mention may be made of salts with inorganic acids such as hydrobromic acid, nitric acid, sulfuric acid, phosphoric acid and the like, or salts with organic acids such as acetic acid, phthalic acid, fumaric acid, oxalic acid, tartaric acid, maleic acid, citric acid, succinic acid, methanesulfonic acid, p-toluenesulfonic acid and the like.

Compounds as provided herein may be either hydrates or non-hydrates. The hydrate may be exemplified by a 0.5-hydrate, a 1-hydrate, a 1.5-hydrate, a 2-hydrate or the like.

If necessary, a compound as herein provided can be obtained as a desired R-isomer or S-isomer, by using a method known per se, such as asymmetric synthesis, optical resolution or the like.

A prodrug of a compound herein provided refers to a compound which is converted to the disclosed compound by an in vivo reaction of enzyme, gastric acid or the like under the physiological conditions, that is, a compound which changes to the disclosed compound upon enzymatic oxidation, reduction, hydrolysis or the like, or a compound which changes to a compound provided herein upon hydrolysis by gastric acid or the like.

The prodrug of a compound provided herein may be exemplified by a compound resulting from acylation, alkylation or phosphorylation of the amino group of the disclosed compound [e.g., a compound in which the amino group of the disclosed compound is in the form of eicosanoyl, alanyl, pentylaminocarbonyl, (5-methyl-2-oxo-1,3-dioxolen-4-yl) methoxycarbonyl, tetrahydrofuranyl, pyrrolidylmethyl, pivaloyloxymethyl, tert-butyl or the like]; a compound resulting from acylation, alkylation, phosphorylation or boration of the hydroxy group of the disclosed compound [e.g., a compound in which the hydroxy group of the disclosed compound is in the form of acetyl, palmitoyl, propanoyl, pivaloyl, succinyl, fumaryl, alanyl, dimethylaminomethylcarbonyl or the like); a compound resulting from esterification or amidation of the carboxy group of the disclosed compound [e.g., a compound in which the carboxy group of the disclosed compound is in the form of ethyl ester, phenyl ester, carboxymethyl ester, dimethylaminomethyl ester, pivaloyloxymethyl ester, ethoxycarbonyloxyethyl ester, phthalidyl ester, (5-methyl-2-oxo-1,3-dioxolen-4-yl)methyl ester, cyclohexyloxycarbonylethyl ester, methylamide or the like); or the like. These compounds can be produced from compounds provided herein by methods known per se in the art. The prodrug of a compound herein provided may also be a compound which changes to the compound provided herein under the physiological conditions.

The compounds provided herein are NPS antagonists that are selective for the NPS receptor with activity as noted above. Ke denotes the molar concentration required to achieve IC50. In some embodiments Ke is 500 nM or less. In certain embodiments that NPSR antagonist is selective for NPS, preventing the binding of NPS and NPSR.

Administering an effective amount of an NPSR antagonist as provided to a subject in need thereof may bind the NPS receptor and produce a therapeutic effect. The subject may be a human or other mammal and may also be a bird, reptile, fish, or amphibian.

The therapeutic effect may include preventing or treating a disease or condition attributable to binding of an agonist to an NPSR. Such diseases or conditions include, by way of non-limiting example, substance abuse, relapse from substance abuse, panic disorders, phobias, post-traumatic stress disorder, and sleep disorders including narcolepsy. Substance abuse may include without limitation opiate addiction, cocaine addiction, nicotine addiction and ethanol addiction.

In certain embodiments the NPSR antagonist as provided herein is used for the manufacture of a prophylactic and/or therapeutic agent for at least one of a disease or condition attributable to binding of an agonist to a neuropeptide-S receptor, including without limitation substance abuse, relapse from substance abuse, panic disorders, phobias, post-traumatic stress disorder, and sleep disorders including narcolepsy.

The NPSR antagonists provided herein may be administered by a variety of methods. Thus, those products that are active by the oral route may be administered in solutions, suspensions, emulsions, tablets, including sublingual and intrabuccal tablets, soft gelatin capsules, including solutions used in soft gelatin capsules, aqueous or oil suspensions, emulsions, pills, capsules, lozenges, troches, tablets, syrups or elixirs and the like. Products of the compounds herein active on parenteral administration may be administered by depot injection, implants including Silastic™ and biodegradable implants, skin patches, skin creams, aerosol, troche, bolus, suppository, or intramuscular and intravenous injections.

Compositions may be prepared according to any method known to the art for the manufacture of pharmaceutical compositions and such compositions may contain one or more agents selected from the group consisting of sweetening agents, flavoring agents, coloring agents and preserving agents. Tablets containing the active ingredient in admixture with nontoxic pharmaceutically acceptable excipients which are suitable for manufacture of tablets are acceptable. These excipients may be, for example, inert diluents, such as calcium carbonate, sodium carbonate, lactose, calcium phosphate or sodium phosphate granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may also be presented as hard gelatin capsules wherein the active ingredient is mixed with an inert solid diluent, for example calcium carbonate, calcium phosphate or kaolin, or as soft gelatin capsules wherein the active ingredient is mixed with water or an oil medium, such as peanut oil, liquid paraffin or olive oil.

Aqueous suspensions of the compounds herein contain the active materials in admixture with excipients suitable for the manufacture of aqueous suspensions. Such excipients include a suspending agent, such as sodium carboxymethylcellulose, methylcellulose, hydroxypropylethyl cellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from a fatty acid and a hexitol anhydride (e.g., polyoxyethylene sorbitan mono-oleate). The aqueous suspension may also contain one or more preservatives such as ethyl or n-propyl p-hydroxybenzoate, one or more coloring agents, one or more flavoring agents and one or more sweetening agents, such as sucrose, aspartame or saccharin. Ophthalmic formulations, as is known in the art, will be adjusted for osmotic pressure.

Oil suspensions may be formulated by suspending the active ingredient in a vegetable oil, such as arachis oil, olive oil, sesame oil or coconut oil, or in a mineral oil such as liquid paraffin. The oil suspensions may contain a thickening agent, such as beeswax, hard paraffin or cetyl alcohol. Sweetening agents may be added to provide a palatable oral preparation. These compositions may be preserved by the addition of an antioxidant such as ascorbic acid.

Dispersible powders and granules of the compounds herein suitable for preparation of an aqueous suspension by the addition of water may be formulated from the active ingredients in admixture with a dispersing, suspending and/or wetting agent, and one or more preservatives. Suitable dispersing or wetting agents and suspending agents are exemplified by those disclosed above. Additional excipients, for example sweetening, flavoring and coloring agents, may also be present.

The pharmaceutical composition of the compounds herein may also be in the form of oil-in-water emulsions. The oily phase may be a vegetable oil, such as olive oil or arachis oil, a mineral oil, such as liquid paraffin, or a mixture of these. Suitable emulsifying agents include naturally occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion may also contain sweetening and flavoring agents.

Syrups and elixirs may be formulated with sweetening agents, such as glycerol, sorbitol or sucrose. Such formulations may also contain a demulcent, a preservative, a flavoring or a coloring agent.

The pharmaceutical compositions of the compounds herein may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a nontoxic parenterally acceptable diluent or solvent, such as a solution of 1,3-butanediol. Among the acceptable vehicles and solvents that may be employed are water and Ringer's solution, an isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables. Sterilization may be performed by conventional methods known to those of ordinary skill in the art such as, for example, by aseptic filtration, or irradiation.

Aqueous formulations (i.e oil-in-water emulsions, syrups, elixirs and injectable preparations) may be formulated to achieve the pH of optimum stability. The determination of the optimum pH may be performed by conventional methods known to those of ordinary skill in the art. Suitable buffers may also be used to maintain the pH of the formulation.

The content of compounds herein in the pharmaceutical composition may vary depending on the form of preparation, but the content may be about 0.01 to 100% by weight, about 0.1 to 50% by weight, and 0.5 to 20% by weight, of the total pharmaceutical composition.

The content of the pharmaceutically acceptable carrier in the pharmaceutical composition may vary depending on the form of preparation, but the content may be about 1 to 99.99% by weight, including all intermediate ranges, of the total pharmaceutical composition.

The compounds of the compounds herein may also be administered in the form of suppositories for rectal administration of the drug. These compositions can be prepared by mixing the drug with a suitable nonirritating excipient which is solid at ordinary temperatures but liquid at rectal temperatures and will therefore melt in the rectum to release the drug. Non-limiting examples of such materials are cocoa butter and polyethylene glycols.

They may also be administered by intranasal, intraocular, intravaginal, and intrarectal routes including suppositories, insufflation, powders and aerosol formulations.

Products of the compounds herein which are preferably administered by the topical route may be administered as applicator sticks, solutions, suspensions, emulsions, gels, creams, ointments, pastes, jellies, paints, powders, and aerosols.

The compounds herein may be administered to any warm-blooded mammal such as humans, domestic pets, and farm animals. Domestic pets include dogs, cats, birds, etc. Farm animals include cows, horses, pigs, sheep, goats, etc.

The amount of active ingredient that may be combined with a carrier material to produce a single dosage form will vary depending upon the disease treated, the mammalian species, and the particular mode of administration.

A therapeutically effective amount may be determined by routine experimentation and by analogy from the amounts used to treat the same disease states with analogous steroid compounds. For example, a unit dose of the steroid may preferably contain between 0.1 milligram and 1 gram of the active ingredient. A unit dose may be between 0.001 and 0.5 grams. It will be understood, however, that the specific dose level for any particular patient will depend on a variety of factors including the activity of the specific compound employed; the age, body weight, general health, sex and diet of the individual being treated the time and route of administration; the rate of excretion: other drugs which have previously been administered; and the severity of the particular disease undergoing therapy, as is well understood by those of skill in the art.

The embodiments may be practiced in other specific forms. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

Compounds as provided herein may be made according to the procedures outlined in FIGS. 1 and 2 and in the examples below.

EXAMPLES

Synthesis

Example 1

Complete Synthesis of R06039-455

1-(4-Fluorophenyl)-3-methylbutan-1-one. To a solution of 4-fluoro-benzonitrile (6 g, 49.5 mmol) in diethyl ether (200 mL) was added i-BuMgCl (1 M soln in THF) and the reaction mixture heated to reflux for 16 hours. The reaction mixture was cooled to room temperature and poured into a mixture 6 N $H_2SO_4$ (60 mL) and ice (500 mL), then stirred at 0° C. for 30 min. The aqueous layer was extracted with ethyl acetate (200 mL), the combined organic layers were washed with brine (100 mL), dried ($MgSO_4$), and concentrated. The residue was purified by column chromatography (80 g, $SiO_2$, 0 to 40% diethyl ether/dichloromethane 1:1 in hexanes) to provide 1-(4-fluorophenyl)-3-methylbutan-1-one as a colorless oil (3.72 g, 42%): $^1$H NMR (300 MHz, CHLOROFORM-d) δ ppm 1.00 (d, J=6.78 Hz, 6H), 2.29 (dt, J=13.47, 6.64 Hz, 1H), 2.81 (d, J=6.78 Hz, 2H), 7.06-7.19 (m, 2H), 7.94-8.02 (m, 2H); MS m/z 172 (Dimer-OH)$^{++}$.

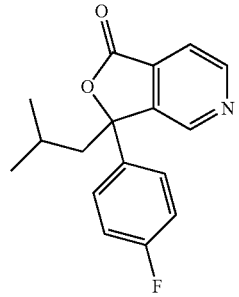

Compound 1

Chemical Formula:
$C_{17}H_{16}FNO_2$
Molecular Weight: 285.31

3-(4-Fluorophenyl)-3-isobutylfuro[3,4-c]pyridin-1(3H)-one. To a solution of 4-diisopropylamidopyridine (3.2 g, 15.54 mmol) in anhydrous diethyl ether (160 mL) at −78° C. was added a 1M solution of LDA in diethyl ether (23.27 mL) and the reaction mixture stirred at −78° C. for 2 hours. A solution of 1-(4-fluorophenyl)-3-methylbutan-1-one (3.5 g, 19.42 mmol) in anhydrous diethyl ether (5 mL) was added dropwise, and the reaction was stirred at −78° C. for 30 min. The reaction mixture was quenched with brine (100 mL), extracted with ethyl acetate (3×50 mL), dried ($MgSO_4$), and concentrated. The crude mixture was stirred with 6 N HCl (50 mL) for 12 hours, then cooled to 0° C. Sodium hydroxyde (15 g, 37.5 mmol) was added in 3 portions, the reaction mixture was stirred at 0° C. for 30 min, then extracted with ethyl acetate (3×100 mL). The organic layers were dried ($MgSO_4$), concentrated and purified by column chromatography (40 g, SiO$_2$, 0 to 40% ethyl acetate in hexanes) to provide 3-(4-fluorophenyl)-3-isobutylfuro[3,4-c]pyridin-1(3H)-one (296 mg, 7%) as an off-white solid. $^1$H NMR (300 MHz, CHLOROFORM-d) δ ppm 0.80-0.91 (m, 6H), 1.54-1.66 (m, 1H), 2.06 (dd, J=14.88, 6.97 Hz, 1H), 2.48 (dd, J=15.07, 5.27 Hz, 1H), 7.04-7.14 (m, 2H), 7.46-7.56 (m, 2H), 7.77 (dd, J=5.09, 0.94 Hz, 1H), 8.85 (d, J=4.90 Hz, 1H), 9.01 (s, 1H); MS m/z 286 (M+H)$^+$.

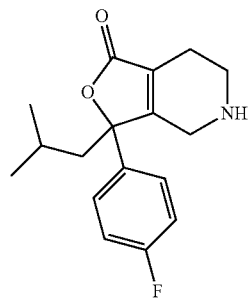

Compound 2

Chemical Formula:
C$_{17}$H$_{20}$FNO$_2$
Molecular Weight: 289.34

3-(4-Fluorophenyl)-3-isobutyl-4,5,6,7-tetrahydrofuro[3,4-c]pyridin-1(3H)-one. To a solution of 3-(4-fluorophenyl)-3-isobutylfuro[3,4-c]pyridin-1(3H)-one (296 mg, 1.04 mmol) in dichloromethane (5 mL) at 0° C. was added 1 N HCl in diethyl ether. The reaction mixture was stirred at 0° C. for 40 min., then filtered and the precipitated hydrochloride salt dried in high vacuo for 1 hour. The precipitate was re-dissolved in ethanol (10 mL), PtO$_2$ (40 mg) was added, and the reaction mixture was hydrogenated at 40 psi for 30 min. The mixture was filtered through a pad of diatomaceous earth, the filtrate concentrated in vacuo. The residue was re-dissolved in dichloromethane (50 mL) and stirred with sat. NaHCO$_3$ soln. for 20 min., then dried (MgSO$_4$) and concentrated. The residue was purified by column chromatography (4 g, SiO$_2$, 0 to 2.5% methanol in dichloromethane) to provide 3-(4-fluorophenyl)-3-isobutyl-4,5,6,7-tetrahydrofuro[3,4-c]pyridin-1(3H)-one (160 mg, 53%): $^1$H NMR (300 MHz, CHLOROFORM-d) δ ppm 0.83-0.98 (m, 6H), 1.56 (br. s., 1H), 1.65 (ddd, J=13.37, 6.59, 5.27 Hz, 1H), 1.72-1.81 (m, 1H), 2.15-2.38 (m, 3H), 2.84-3.05 (m, 2H), 3.34-3.50 (m, 1H), 3.58-3.73 (m, 1H), 7.00-7.12 (m, 2H), 7.27-7.34 (m, 2H); MS m/z 290 (M+H)$^+$, 288 (M–H)$^-$.

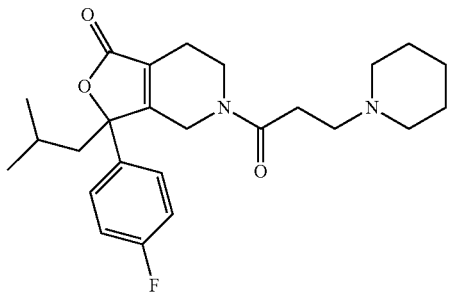

R06039-455

Chemical Formula: C$_{25}$H$_{33}$FN$_2$O$_3$
Molecular Weight: 428.54

3-(4-Fluorophenyl)-3-isobutyl-5-(3-(piperidin-1-yl)propanoyl)-4,5,6,7-tetrahydrofuro[3,4-c]pyridin-1(3H)-one. The procedure described for R06039-421 was employed to convert 3-(piperidin-1-yl)propanoic acid (174 mg, 1.106 mmol) and 3-(4-fluorophenyl)-3-isobutyl-4,5,6,7-tetrahydrofuro[3,4-c]pyridin-1(3H)-one (160 mg, 0.553 mmol) to 3-(4-fluorophenyl)-3-isobutyl-5-(3-(piperidin-1-yl)propanoyl)-4,5,6,7-tetrahydrofuro[3,4-c]pyridin-1(3H)-one (64 mg, 27%). The desired product was purified by column chromatography (12 g, SiO$_2$, 0 to 2.5% methanol in dichloromethane) and semi-preparative HPLC: $^1$H NMR (300 MHz, CHLOROFORM-d) δ ppm 0.80-0.99 (m, 6H), 1.56-1.71 (m, 7H), 1.78 (dd, J=14.51, 7.35 Hz, 1H), 2.27 (dd, J=14.69, 4.90 Hz, 1H), 2.37-2.59 (m, 6H), 2.62-2.83 (m, 5H), 3.41 (dt, J=13.37, 6.50 Hz, 1H), 3.66-3.79 (m, 1H), 3.96 (d, J=19.59 Hz, 1H), 4.65 (d, J=19.59 Hz, 1H), 7.01-7.15 (m, 2H), 7.28-7.38 (m, 2H); $^{19}$F NMR (282 MHz, CHLOROFORM-d) δ ppm –113.6; MS m/z 429 (M+H)$^+$; HPLC>96.8% (AUC), t$_R$=26.24 min(5 to 66% CH$_3$CN over 30 min).

Example 2

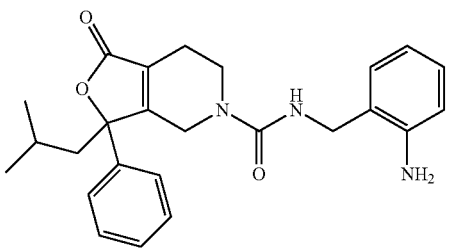

R06039-275

Chemical Formula: C$_{25}$H$_{29}$N$_3$O$_3$
Molecular Weight: 419.52

N-(2-aminobenzyl)-3-isobutyl-1-oxo-3-phenyl-3,4,6,7-tetrahydrofuro[3,4-c]pyridine-5(1H)-carboxamide. To an ice-cold solution of triphosgene (36 mg, 0.123 mmol) and triethyl amine (75 mg, 0.737 mmol) in anhydrous THF (15 mL) was added tert-butyl 2-(aminomethyl)phenylcarbamate (100 mg, 0.369 mmol) in anhydrous THF (2 mL). The reaction mixture was stirred at 0° C. for 15 min., then warmed to room temperature and concentrated to dryness. The residue was re-dissolved in anhydrous dichloromethane (15 mL), a solution of 3-isobutyl-3-phenyl-4,5,6,7-tetrahydrofuro[3,4-c]pyridin-1(3H)-one (100 mg, 0.369 mmol) (prepared according to the methods described for 3-(4-fluorophenyl)-3-isobutyl-4,5,6,7-tetrahydrofuro[3,4-c]pyridin-1(3H)-one, Scheme 1) in anhydrous dichloromethane (2 mL) was added, and the mixture stirred at room temperature for 16 hours. The reaction mixture was concentrated and purified by column chromatography (12 g, SiO$_2$, 0 to 30% ethyl acetate in hexanes) to provide tert-butyl 2-((3-isobutyl-1-oxo-3-phenyl-1,3,4,5,6,7-hexahydrofuro[3,4-c]pyridine-5-carboxamido)methyl)phenylcarbamate as a colorless oil (68 mg, 21% yield). $^1$H NMR (300 MHz, CHLOROFORM-d) δ ppm 0.78-0.97 (m, 6H), 1.50-1.55 (m, 9H), 1.55-1.69 (m, 1H), 1.77 (dd, J=14.51, 7.35 Hz, 1H), 2.22-2.42 (m, 3H), 3.12-3.46 (m, 1H), 3.50-3.63 (m, 1H), 3.88 (d, J=18.84 Hz, 1H), 3.89-3.90 (m, 1H), 4.25-4.36 (m, 2H), 4.44 (d, J=18.84 Hz, 1H), 5.78 (d, J=5.65 Hz, 1H), 7.01 (dd, J=7.54, 1.13 Hz, 1H), 7.14-7.26 (m, 2H), 7.26-7.42 (m, 4H), 7.69 (d, J=8.29 Hz, 1H), 8.46-8.57 (m, 1H); MS m/z 542 (M+Na)⁺, 518 (M−H)⁻.

Example 3

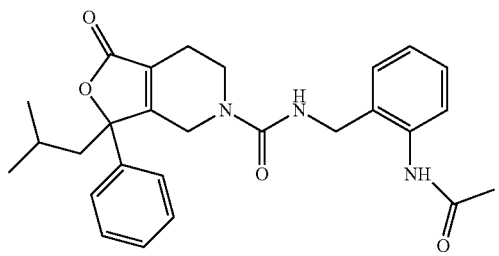

R06039-409

Chemical Formula: C₂₇H₃₁N₃O₄
Molecular Weight: 461.55

3-Isobutyl-1-oxo-3-phenyl-N-(2-(3-(piperidin-1-yl)propanamido)benzyl)-3,4,6,7-tetrahydrofuro[3,4-c]pyridine-5 (1H)-carboxamide. The procedure described for R06039-409 was employed to convert 3-(piperidin-1-yl)propanoyl chloride (35 mg, 0.059 mmol) to 3-isobutyl-1-oxo-3-phenyl-N-(2-(3-(piperidin-1-yl)propanamido)benzyl)-3,4,6,7-tetrahydrofuro[3,4-c]pyridine-5(1H)-carboxamide (34 mg, 71%): ¹H NMR (300 MHz, DMSO-d₆) δ ppm 0.74-0.91 (m, 6H), 1.30-1.55 (m, 8H), 1.80-1.97 (m, 1H), 2.16-2.41 (m, 10H), 2.57 (t, J=6.59 Hz, 1H), 2.78-3.13 (m, 1H), 3.55-3.77 (m, 1H), 3.80-3.99 (m, 1H), 4.23 (d, J=5.65 Hz, 2H), 4.37-4.57 (m, 1H), 7.08 (s, 1H), 7.20 (dd, J=4.90, 2.26 Hz, 1H), 7.28-7.54 (m, 6H), 7.68 (s, 1H), 10.09 (s, 1H); MS m/z 559 (M+H)⁺, 558 (M−H)⁻.

Example 4

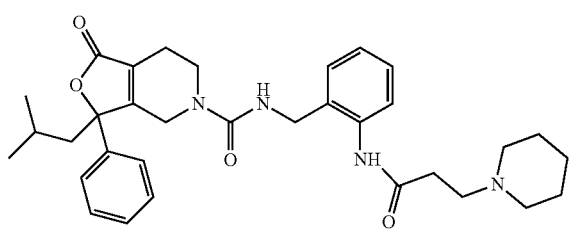

R06039-410

Chemical Formula: C₃₃H₄₂N₄O₄
Molecular Weight: 558.71

3-Isobutyl-1-oxo-3-phenyl-N-(2-(3-(piperidin-1-yl)propanamido)benzyl)-3,4,6,7-tetrahydrofuro[3,4-c]pyridine-5 (1H)-carboxamide. The procedure described for R06039-409 was employed to convert 3-(piperidin-1-yl)propanoyl chloride (35 mg, 0.059 mmol) to 3-isobutyl-1-oxo-3-phenyl-N-(2-(3-(piperidin-1-yl)propanamido)benzyl)-3,4,6,7-tetrahydrofuro[3,4-c]pyridine-5(1H)-carboxamide (34 mg, 71%): ¹H NMR (300 MHz, DMSO-d₆) δ ppm 0.74-0.91 (m, 6H), 1.30-1.55 (m, 8H), 1.80-1.97 (m, 1H), 2.16-2.41 (m, 10H), 2.57 (t, J=6.59 Hz, 1H), 2.78-3.13 (m, 1H), 3.55-3.77 (m, 1H), 3.80-3.99 (m, 1H), 4.23 (d, J=5.65 Hz, 2H), 4.37-4.57 (m, 1H), 7.08 (s, 1H), 7.20 (dd, J=4.90, 2.26 Hz, 1H), 7.28-7.54 (m, 6H), 7.68 (s, 1H), 10.09 (s, 1H); MS m/z 559 (M+H)⁺, 558 (M−H)⁻.

Example 5

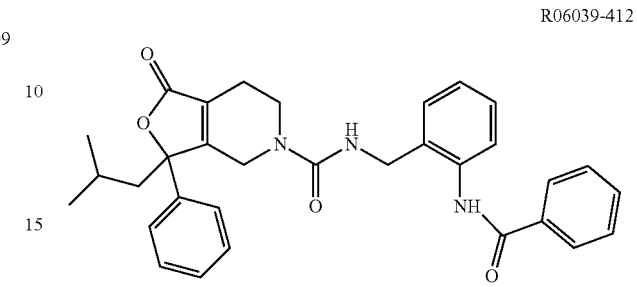

R06039-412

Chemical Formula: C₃₂H₃₃N₃O₄
Molecular Weight: 523.62

N-(2-Benzamidobenzyl)-3-isobutyl-1-oxo-3-phenyl-3,4,6,7-tetrahydrofuro[3,4-c]pyridine-5(1H)-carboxamide. The procedure described for R06039-409 was employed to convert benzoyl chloride (18 mg, 0.13 mmol) to N-(2-benzamidobenzyl)-3-isobutyl-1-oxo-3-phenyl-3,4,6,7-tetrahydrofuro[3,4-c]pyridine-5(1H)-carboxamide (24 mg, 39%): ¹H NMR (300 MHz, CHLOROFORM-d) δ ppm 0.81-0.96 (m, 6H), 1.57-1.72 (m, 1H), 1.72-1.86 (m, 1H), 1.72-1.87 (m, 1H), 2.21-2.48 (m, 2H), 3.20-3.36 (m, 1H), 3.50 (m, J=13.60 Hz, 1H), 3.67-3.75 (m, 1H), 3.88 (d, J=18.84 Hz, 1H), 4.28-4.46 (m, 2H), 5.16-5.28 (m, 1H), 7.17 (dd, J=7.35, 1.32 Hz, 1H), 7.27-7.44 (m, 7H), 7.45-7.65 (m, 3H), 7.90-8.00 (m, 1H), 8.05-8.16 (m, 2H), 10.28 (s, 1H); MS m/z 524 (M+H)⁺, 546 (M+23)⁺, 522 (M−H).

Example 6

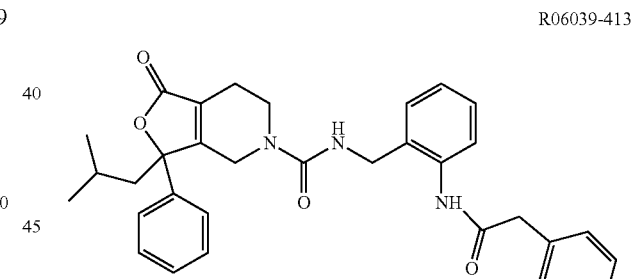

R06039-413

Chemical Formula: C₃₃H₃₅N₃O₄
Molecular Weight: 537.65

3-Isobutyl-1-oxo-3-phenyl-N-(2-(2-phenylacetamido) benzyl)-3,4,6,7-tetrahydrofuro[3,4-c]pyridine-5(1H)-carboxamide. To an ice-cold solution of tert-butyl 2-((3-isobutyl-1-oxo-3-phenyl-1,3,4,5,6,7-hexahydrofuro[3,4-c] pyridine-5-carboxamido)methyl)phenylcarbamate (62 mg, 0.119 mmol) in dichloromethane (5 mL) was added TFA (1 mL). The reaction mixture stirred at 0° C. for 5 hours and concentrated to dryness to provide crude N-(2-aminobenzyl)-3-isobutyl-1-oxo-3-phenyl-3,4,6,7-tetrahydrofuro[3,4-c]pyridine-5(1H)-carboxamide. The residue was added to a solution of 2-phenylacetic acid (32 mg, 0.238 mmol), BOP (79 mg, 0.179 mmol), and N,N'-diisopropylethylamine (62 mg, 0.477 mmol) in dichloromethane (5 mL), and stirred at room temperature for 16 hours. The crude reaction mixture was concentrated to dryness and purified by column chromatography (12 g, SiO₂, 0 to 100% ethyl acetate in hexanes) to provide 3-isobutyl-1-oxo-3-phenyl-N-(2-(2-phenylacetamido)benzyl)-3,4,6,7-tetrahydrofuro[3,4-c]pyridine-5(1H)-carboxamide (66 mg, 93%) as a colorless oil: $^1$H NMR (300 MHz, CHLOROFORM-d) δ ppm 0.81-0.98 (m, 6H), 1.65 (dd, J=11.87, 6.59 Hz, 1H), 1.73-1.84 (m, 1H), 2.24-2.47 (m, 4H), 3.30 (dt, J=13.19, 6.22 Hz, 1H), 3.52 (dt, J=13.56, 5.09 Hz, 1H), 3.75 (s, 2H), 3.91 (d, J=18.84 Hz, 1H), 4.21-4.48 (m, 2H), 5.22 (br. s., 1H), 6.97-7.09 (m, 1H), 6.99-7.10 (m, 1H), 7.18 (d, J=6.78 Hz, 1H), 7.23-7.47 (m, 9H), 7.75 (br. s., 1H), 7.96 (d, J=7.91 Hz, 1H), 9.65 (br. s., 1H); MS m/z 538 (M+H)$^+$, 560 (M+23)$^+$, 536 (M−H)$^−$.

Example 7

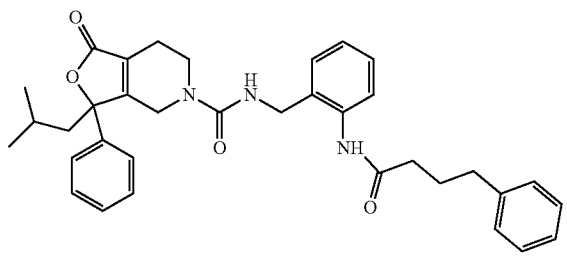

Chemical Formula: C$_{35}$H$_{39}$N$_3$O$_4$
Molecular Weight: 565.70

3-isobutyl-1-oxo-3-phenyl-N-(2-(4-phenylbutanamido)benzyl)-3,4,6,7-tetrahydrofuro[3,4-c]pyridine-5(1H)-carboxamide. The procedure described for R06039-413 was employed to convert 4-phenylbutanoic acid (32 mg, 0.191 mmol) to 3-isobutyl-1-oxo-3-phenyl-N-(2-(4-phenylbutanamido)benzyl)-3,4,6,7-tetrahydrofuro[3,4-c]pyridine-5(1H)-carboxamide: (39 mg, 72%): $^1$H NMR (300 MHz, CHLOROFORM-d) δ ppm 0.83-0.96 (m, 6H), 1.56-1.70 (m, 1H), 1.71-1.85 (m, 1H), 1.99-2.15 (m, 2H), 2.23-2.41 (m, 3H), 2.43-2.53 (m, 2H), 2.68-2.77 (m, 2H), 3.22-3.33 (m, 1H), 3.51 (dt, J=13.56, 5.27 Hz, 1H), 3.83-3.93 (m, 1H), 4.27-4.44 (m, 3H), 5.23 (d, J=4.90 Hz, 1H), 7.01-7.11 (m, 1H), 7.13-7.41 (m, 12H), 8.05 (d, J=7.91 Hz, 1H), 9.68 (s, 1H); MS m/z 566 (M+H)$^+$, 566 (M+23)$^+$, 564 (M−H)$^+$.

Example 8

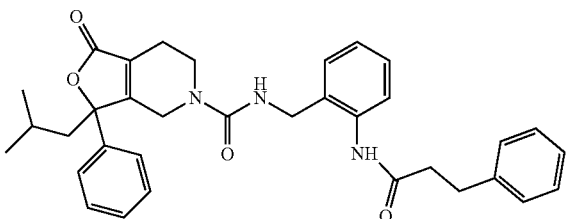

Chemical Formula: C$_{34}$H$_{37}$N$_3$O$_4$
Molecular Weight: 551.68

3-Isobutyl-1-oxo-3-phenyl-N-(2-(3-phenylpropanamido)benzyl)-3,4,6,7-tetrahydrofuro[3,4-c]pyridine-5(1H)-carboxamide. The procedure described for R06039-413 was employed to convert 3-phenylpropionic acid (29 mg, 0.191 mmol) 3-isobutyl-1-oxo-3-phenyl-N-(2-(3-phenylpropanamido)benzyl)-3,4,6,7-tetrahydrofuro[3,4-c]pyridine-5 (1H)-carboxamide (34 mg, 71%): $^1$H NMR (300 MHz, CHLOROFORM-d) δ ppm 0.80-0.97 (m, 6H), 1.59-1.70 (m, 1H), 1.75 (d, J=14.32 Hz, 1H), 2.21-2.48 (m, 2H), 2.71-2.81 (m, 2H), 3.02-3.11 (m, 2H), 3.21-3.33 (m, 1H), 3.49 (d, J=13.56 Hz, 2H), 3.89 (s, 1H), 4.20-4.44 (m, 3H), 5.02-5.13 (m, 1H), 7.06 (d, J=1.13 Hz, 1H), 7.14-7.39 (m, 12H), 8.05 (s, 1H), 9.72 (s, 1H); MS m/z 553 (M+H)$^+$, 575 (M+23)$^+$, 551 (M−H)$^−$.

Example 9

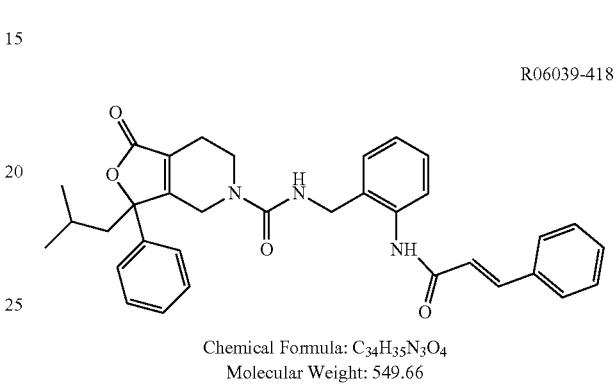

Chemical Formula: C$_{34}$H$_{35}$N$_3$O$_4$
Molecular Weight: 549.66

(E)-N-(2-cinnamamidobenzyl)-3-isobutyl-1-oxo-3-phenyl-3,4,6,7-tetrahydrofuro[3,4-c]pyridine-5(1H)-carboxamide. The procedure described for R06039-413 was employed to convert trans-phenyl propenoic acid (21 mg, 0.143 mmol) to (E)-N-(2-cinnamamidobenzyl)-3-isobutyl-1-oxo-3-phenyl-3,4,6,7-tetrahydrofuro[3,4-c]pyridine-5(1H)-carboxamide: (31 mg, 79%): $^1$H NMR (300 MHz, CHLOROFORM-d) δ ppm 0.78-0.97 (m, 6H), 1.59-1.69 (m, 1H), 1.69-1.84 (m, 1H), 2.25 (dd, J=14.51, 4.71 Hz, 1H), 2.31-2.50 (m, 2H), 3.24-3.39 (m, 1H), 3.54 (dt, J=13.56, 5.09 Hz, 2H), 3.92 (dt, J=18.84, 2.64 Hz, 1H), 4.46 (dd, J=6.40, 1.88 Hz, 2H), 5.16 (br. s., 1H), 6.86 (d, J=15.45 Hz, 1H), 7.02-7.12 (m, 1H), 7.16-7.50 (m, 10H), 7.57-7.66 (m, 2H), 7.76 (d, J=15.82 Hz, 1H), 8.31 (d, J=7.91 Hz, 1H), 10.05 (br. s., 1H); MS m/z 551 (M+H)$^+$, 573 (M+23)$^+$, 549 (M−H)$^−$.

Example 10

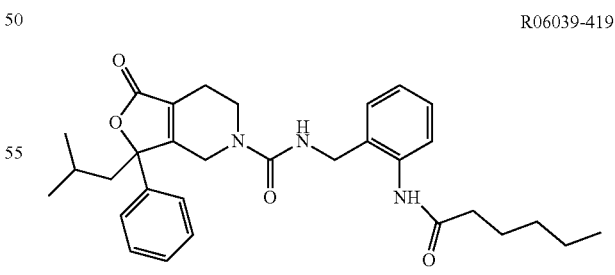

Chemical Formula: C$_{31}$H$_{39}$N$_3$O$_4$
Molecular Weight: 517.66

N-(2-Hexanamidobenzyl)-3-isobutyl-1-oxo-3-phenyl-3,4,6,7-tetrahydrofuro[3,4-c]pyridine-5(1H)-carboxamide. The procedure described for R06039-413 was employed to convert hexanoic acid (17 mg, 0.143 mmol) to N-(2-hexanamidobenzyl)-3-isobutyl-1-oxo-3-phenyl-3,4,6,7-tetrahydrofuro[3,4-c]pyridine-5(1H)-carboxamide (28 mg, 76%): $^1$H NMR (300 MHz, CHLOROFORM-d) δ ppm 0.81-0.98 (m, 9H), 1.33-1.43 (m, 4H), 1.61-1.85 (m, 4H), 2.26-2.46 (m, 5H), 3.22-3.39 (m, 1H), 3.46-3.61 (m, 1H), 3.82-3.96 (m, 1H), 4.28-4.48 (m, 3H), 5.16 (br. s., 1H), 7.07 (d, J=7.16 Hz, 1H), 7.20 (dd, J=7.54, 1.51 Hz, 1H), 7.24-7.46 (m, 6H), 8.07 (d, J=8.29 Hz, 1H), 9.58 (br. s., 1H); MS m/z 519 (M+H)$^+$, 540 (M+23)$^+$, 517 (M−H)$^−$.

Example 11

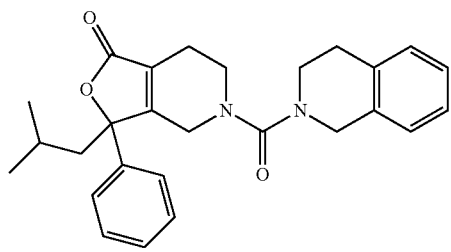

R06039-411

Chemical Formula: $C_{27}H_{30}N_2O_3$
Molecular Weight: 430.54

3-isobutyl-3-phenyl-5-(1,2,3,4-tetrahydroisoquinoline-2-carbonyl)-4,5,6,7-tetrahydrofuro[3,4-c]pyridin-1(3H)-one. The procedure described for R06039-275 was employed to convert 1,2,3,4-tetrahydroisoquinoline hydrochloride (130 mg, 0.766 mmol) to 3-isobutyl-3-phenyl-5-(1,2,3,4-tetrahydroisoquinoline-2-carbonyl)-4,5,6,7-tetrahydrofuro[3,4-c]pyridin-1(3H)-one (27 mg, 8%): $^1$H NMR (300 MHz, CHLOROFORM-d) δ ppm 0.81-0.99 (m, 6H), 1.66 (dd, J=6.78, 4.90 Hz, 1H), 1.75-1.86 (m, 1H), 2.29 (dd, J=14.69, 4.90 Hz, 1H), 2.47 (td, J=4.99, 2.45 Hz, 2H), 2.90 (t, J=5.65 Hz, 2H), 3.29 (dd, J=6.78, 4.90 Hz, 1H), 3.36-3.48 (m, 1H), 3.51 (t, J=5.84 Hz, 1H), 3.77-3.90 (m, 1H), 4.12-4.23 (m, 1H), 4.43 (s, 2H), 7.07 (dd, J=5.27, 3.77 Hz, 1H), 7.12-7.22 (m, 3H), 7.28-7.44 (m, 5H); MS m/z 431 (M+H)$^+$, 453 (M+23)$^+$, 429 (M−H)$^−$.

Example 12

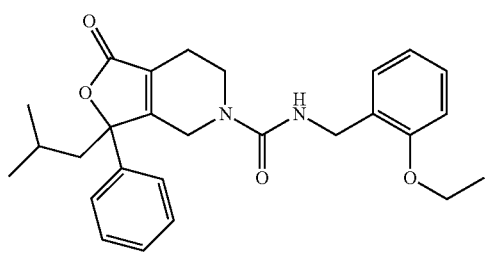

R06039-416

Chemical Formula: $C_{27}H_{32}N_2O_4$
Molecular Weight: 448.55

N-(2-Ethoxybenzyl)-3-isobutyl-1-oxo-3-phenyl-3,4,6,7-tetrahydrofuro[3,4-c]pyridine-5(1H)-carboxamide. To a solution of 2-(2-nitrophenyl)acetic acid (79 mg, 0.435 mmol), 3-isobutyl-3-phenyl-4,5,6,7-tetrahydrofuro[3,4-c]pyridin-1(3H)-one (50 mg, 0.184 mmol), and N,N'-diisopropylethylamine (112 mg, 0.870 mmol) in THF (5 mL) was added BOP reagent (144 mg, 0.326 mmol) and the mixture was stirred at room temperature for 16 hours. The crude reaction mixture was concentrated to dryness and purified by column chromatography (12 g, SiO$_2$, 0 to 100% ethyl acetate in hexanes) to provide 3-isobutyl-5-(2-(2-nitrophenyl)acetyl)-3-phenyl-4,5,6,7-tetrahydrofuro[3,4-c]pyridin-1(3H)-one (57 mg, 60%) as a white solid: $^1$H NMR (300 MHz, CHLOROFORM-d) δ ppm 0.80-1.01 (m, 6H), 1.54-1.73 (m, 1H), 1.74-1.87 (m, 1H), 2.20-2.36 (m, 1H), 2.37-2.63 (m, 2H), 3.42-3.58 (m, 1H), 3.76-3.92 (m, 1H), 3.93-4.14 (m, 2H), 4.40 (m, 1H), 4.75 (d, J=19.59 Hz, 1H), 7.19-7.42 (m, 6H), 7.42-7.53 (m, 1H), 7.53-7.64 (m, 1H), 8.04-8.16 (m, 1H); MS m/z 435 (M+H)$^+$, 457 (M+23)$^+$, 433 (M−H)$^−$.

Example 13

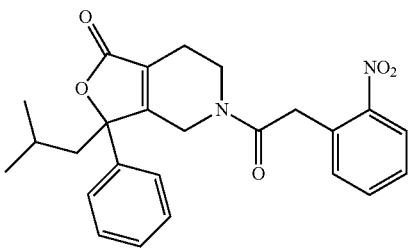

R06039-421

Chemical Formula: $C_{25}H_{26}N_2O_5$
Molecular Weight: 434.48

3-Isobutyl-5-(2-(2-nitrophenyl)acetyl)-3-phenyl-4,5,6,7-tetrahydrofuro[3,4-c]pyridin-1(3H)-one. To a solution of 2-(2-nitrophenyl)acetic acid (79 mg, 0.435 mmol), 3-isobutyl-3-phenyl-4,5,6,7-tetrahydrofuro[3,4-c]pyridin-1(3H)-one (50 mg, 0.184 mmol), and N,N'-diisopropylethylamine (112 mg, 0.870 mmol) in THF (5 mL) was added BOP reagent (144 mg, 0.326 mmol) and the mixture was stirred at room temperature for 16 hours. The crude reaction mixture was concentrated to dryness and purified by column chromatography (12 g, SiO$_2$, 0 to 100% ethyl acetate in hexanes) to provide 3-isobutyl-5-(2-(2-nitrophenyl)acetyl)-3-phenyl-4,5,6,7-tetrahydrofuro[3,4-c]pyridin-1(3H)-one (57 mg, 60%) as a white solid: $^1$H NMR (300 MHz, CHLOROFORM-d) δ ppm 0.80-1.01 (m, 6H), 1.54-1.73 (m, 1H), 1.74-1.87 (m, 1H), 2.20-2.36 (m, 1H), 2.37-2.63 (m, 2H), 3.42-3.58 (m, 1H), 3.76-3.92 (m, 1H), 3.93-4.14 (m, 2H), 4.40 (m, 1H), 4.75 (d, J=19.59 Hz, 1H), 7.19-7.42 (m, 6H), 7.42-7.53 (m, 1H), 7.53-7.64 (m, 1H), 8.04-8.16 (m, 1H); MS m/z 435 (M+H)$^+$, 457 (M+23)$^+$, 433 (M−H)$^−$.

Example 14

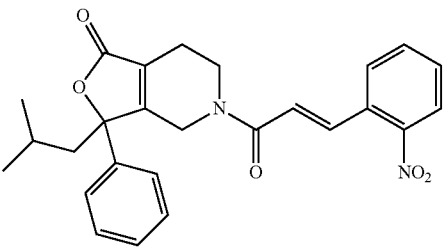

R06039-422

Chemical Formula: $C_{26}H_{26}N_2O_5$
Molecular Weight: 446.50

(E)-3-Isobutyl-5-(3-(2-nitrophenyl)acryloyl)-3-phenyl-4,5,6,7-tetrahydrofuro[3,4-c]pyridin-1(3H)-one. The procedure described for R06039-421 was employed to convert E-3-(2-nitrophenyl)acrylic acid (84 mg, 0.435 mmol) to (E)-3-isobutyl-5-(3-(2-nitrophenyl)acryloyl)-3-phenyl-4,5,6,7-tetrahydrofuro[3,4-c]pyridin-1(3H)-one (90 mg, 92%): $^1$H NMR (300 MHz, CHLOROFORM-d) δ ppm 0.82-0.89 (m, 3H), 0.92-1.00 (m, 3H), 1.54-1.77 (m, 1H), 1.79-1.90 (m, 1H), 2.35 (dd, J=14.51, 4.71 Hz, 1H), 2.49 (br. s., 2H), 3.45-3.64 (m, 1H), 3.83-3.99 (m, 1H), 4.02-4.19 (m, 1H), 4.81 (d, J=19.59 Hz, 1H), 6.72 (d, J=15.45 Hz, 1H), 7.30-7.46 (m, 5H), 7.49-7.71 (m, 3H), 7.97 (d, J=15.45 Hz, 1H), 8.06 (d, J=7.91 Hz, 1H); MS m/z 447 (M+H)$^+$, 469 (M+23)$^+$, 445 (M−H)$^−$.

Example 15

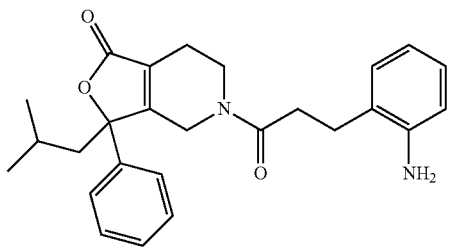

R06039-423

Chemical Formula: $C_{26}H_{30}N_2O_3$
Molecular Weight: 418.53

5-(3-(2-Aminophenyl)propanoyl)-3-isobutyl-3-phenyl-4,5,6,7-tetrahydrofuro[3,4-c]pyridin-1(3H)-one. To a solution of (E)-3-isobutyl-5-(3-(2-nitrophenyl)acryloyl)-3-phenyl-4,5,6,7-tetrahydrofuro[3,4-c]pyridin-1(3H)-one (90 mg, 0.20 mmol) in ethanol/ethyl acetate/(3:1, 20 mL) was added Pd/C (10%, 20 mg). The reaction mixture was stirred vigorously under an atmosphere of H$_2$(g) at room temperature for 1 h. The mixture was filtered through a pad of diatomaceous earth, the filtrate concentrated in vacuo, and the residue purified by column chromatography (4 g, SiO$_2$, 0 to 50% ethyl acetate in hexanes) to provide 5-(3-(2-aminophenyl)propanoyl)-3-isobutyl-3-phenyl-4,5,6,7-tetrahydrofuro[3,4-c]pyridin-1(3H)-one (54 mg, 64%): $^1$H NMR (300 MHz, CHLOROFORM-d) δ ppm 0.82-0.98 (m, 6H), 1.59-1.71 (m, 1H), 1.73-1.87 (m, 1H), 2.18-2.37 (m, 2H), 2.72 (d, J=6.78 Hz, 2H), 2.87 (d, J=6.78 Hz, 2H), 3.22-3.33 (m, 1H), 3.46-3.66 (m, 2H), 3.77-3.89 (m, 2H), 3.92-4.04 (m, 1H), 4.60-4.74 (m, 1H), 6.59-6.64 (m, 2H), 6.96-7.07 (m, 2H), 7.28-7.44 (m, 5H); MS m/z 419 (M+H)$^+$.

Example 16

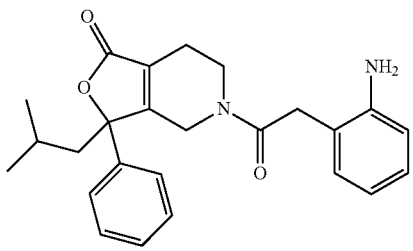

R06039-424

Chemical Formula: $C_{25}H_{28}N_2O_3$
Molecular Weight: 404.50

5-(2-(2-Aminophenyl)acetyl)-3-isobutyl-3-phenyl-4,5,6,7-tetrahydrofuro[3,4-c]pyridin-1(3H)-one. The procedure described for R06039-423 was employed to convert 3-isobutyl-5-(2-(2-nitrophenyl)acetyl)-3-phenyl-4,5,6,7-tetrahydrofuro[3,4-c]pyridin-1(3H)-one to 5-(2-(2-aminophenyl)acetyl)-3-isobutyl-3-phenyl-4,5,6,7-tetrahydrofuro[3,4-c]pyridin-1(3H)-one (40 mg, 75%): $^1$H NMR (300 MHz, CHLOROFORM-d) δ ppm 0.80-0.96 (m, 6H), 1.58-1.70 (m, 1H), 1.72-1.85 (m, 1H), 2.14-2.40 (m, 2H), 3.43 (ddd, J=13.56, 7.91, 5.27 Hz, 1H), 3.70 (s, 2H), 3.80-4.02 (m, 2H), 4.07 (s, 1H), 4.32 (br. s., 2H), 4.73 (d, J=19.59 Hz, 1H), 6.64-6.75 (m, 2H), 6.97-7.12 (m, 2H), 7.29-7.45 (m, 5H); MS m/z 405 (M+H)$^+$, 427 (M+23)$^+$, 403 (M−H)$^−$.

Example 17

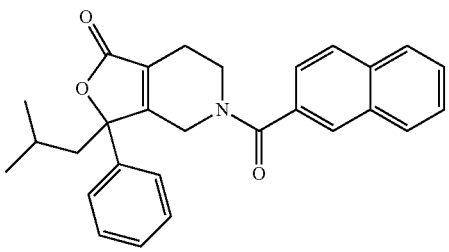

R06039-427

Chemical Formula: $C_{28}H_{27}NO_3$
Molecular Weight: 425.52

5-(2-Naphthoyl)-3-isobutyl-3-phenyl-4,5,6,7-tetrahydrofuro[3,4-c]pyridin-1(3H)-one. To a solution of 3-isobutyl-3-phenyl-4,5,6,7-tetrahydrofuro[3,4-c]pyridin-1(3H)-one (50 mg, 0.184 mmol) and N,N'-diisopropylethylamine (71 mg, 0.552 mmol) in THF (5 mL) at 0° C. was added 2-naphthoyl-chloride (35 mg, 0.184 mmol) and the reaction mixture was stirred at 0° C. for 30 min, then room temperature overnight. The crude mixture was concentrated to dryness and purified by column chromatography (4 g, SiO$_2$, 0 to 30% ethyl acetate in hexanes) to provide 5-(2-naphthoyl)-3-isobutyl-3-phenyl-4,5,6,7-tetrahydrofuro[3,4-c]pyridin-1(3H)-one (68 mg, 87%) as a white solid: $^1$H NMR (300 MHz, CHLOROFORM-d) δ ppm 0.77-1.08 (m, 6H), 1.63-1.78 (m, 1H), 1.79-1.95 (m, 1H), 2.28-2.59 (m, 3H), 3.28-3.60 (m, 1H), 3.73 (br. s., 1H), 4.09-4.27 (m, 1H), 4.85 (br. s., 1H), 7.29-7.51 (m, 6H), 7.52-7.62 (m, 2H), 7.77-7.98 (m, 4H); MS m/z 426 (M+H)$^+$, 449 (M+23)$^+$, 424 (M−H)$^−$.

Example 18

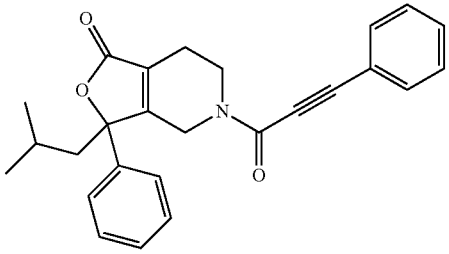

R06039-428

Chemical Formula: $C_{26}H_{25}NO_3$
Molecular Weight: 399.48

3-Isobutyl-3-phenyl-5-(3-phenylpropioloyl)-4,5,6,7-tetrahydrofuro[3,4-c]pyridin-1(3H)-one. The procedure described for R06039-421 was employed to convert 3-phenylpropiolic acid (54 mg, 0.369 mmol) to 3-isobutyl-3-phenyl-5-(3-phenylpropioloyl)-4,5,6,7-tetrahydrofuro[3,4-c]pyridin-1(3H)-one (30 mg, 41%): $^1$H NMR (300 MHz, CHLOROFORM-d) δ ppm 0.84-0.99 (m, 6H), 1.60-1.75 (m, 1H), 1.77-1.93 (m, 1H), 2.27-2.38 (m, 1H), 2.42-2.56 (m, 2H), 3.68 (ddd, J=13.37, 7.72, 5.27 Hz, 1H), 3.98-4.09 (m, 1H), 4.16-4.26 (m, 1H), 4.72-4.84 (m, 1H), 7.29-7.50 (m, 9H), 7.52-7.62 (m, 1H); MS m/z 400 (M+H)$^+$, 422 (M+23)$^+$, 398 (M–H)$^-$.

Example 19

R06039-429

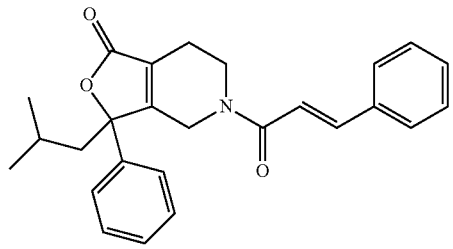

Chemical Formula: $C_{26}H_{27}NO_3$
Molecular Weight: 401.50

5-Cinnamoyl-3-isobutyl-3-phenyl-4,5,6,7-tetrahydrofuro[3,4-c]pyridin-1(3H)-one. The procedure described for R06039-421 was employed to convert cinnamic acid (55 mg, 0.369 mmol) to 5-cinnamoyl-3-isobutyl-3-phenyl-4,5,6,7-tetrahydrofuro[3,4-c]pyridin-1(3H)-one: $^1$H NMR (300 MHz, CHLOROFORM-d) δ ppm 0.81-0.99 (m, 6H), 1.56-1.74 (m, 1H), 1.84 (dd, J=14.69, 7.16 Hz, 1H), 2.35 (dd, J=14.51, 4.71 Hz, 1H), 2.48 (d, J=1.88 Hz, 2H), 3.51 (d, J=5.27 Hz, 1H), 3.93 (dt, J=9.04, 4.52 Hz, 1H), 4.01-4.12 (m, 1H), 4.85 (d, J=19.59 Hz, 1H), 6.87 (d, J=15.45 Hz, 1H), 7.28-7.45 (m, 8H), 7.47-7.60 (m, 2H), 7.69 (d, J=15.45 Hz, 1H); MS m/z 402 (M+H)$^+$, 424 (M+23)$^+$, 400 (M–H)$^-$.

Example 20

R06039-432

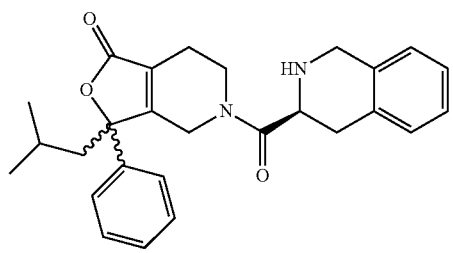

Chemical Formula: $C_{27}H_{30}N_2O_3$
Molecular Weight: 430.54

3-Isobutyl-3-phenyl-5-((S)-1,2,3,4-tetrahydroisoquinoline-3-carbonyl)-4,5,6,7-tetrahydrofuro[3,4-c]pyridin-1(3H)-one. To a solution of (S)-2-(((9H-fluoren-9-yl)methoxy)carbonyl)-1,2,3,4-tetrahydroisoquinoline-3-carboxylic acid (147 mg, 0.369 mmol), 3-isobutyl-3-phenyl-4,5,6,7-tetrahydrofuro[3,4-c]pyridin-1(3H)-one (50 mg, 0.184 mmol), and N,N'-diisopropylethylamine (112 mg, 0.870 mmol) in THF (5 mL) was added BOP reagent (144 mg, 0.326 mmol) and the mixture was stirred at room temperature for 16 hours. The reaction mixture was concentrated to dryness, re-dissolved in 20% piperidine in DMF (5 mL), and stirred at room temperature for 1 hour. The crude reaction mixture was concentrated and purified by column chromatography (12 g, SiO$_2$, 0 to 100% ethyl acetate in hexanes) to provide 3-isobutyl-3-phenyl-5-((S)-1,2,3,4-tetrahydroisoquinoline-3-carbonyl)-4,5,6,7-tetrahydrofuro[3,4-c]pyridin-1(3H)-one (54 mg, 68%) as a mixture of diastereoisomers in form of white solid: $^1$H NMR (300 MHz, CHLOROFORM-d) δ ppm 0.81-1.01 (m, 6H), 1.59-1.74 (m, 1H), 1.75-1.88 (m, 1H), 2.26-2.52 (m, 3H), 2.71-2.85 (m, 1H), 2.87-3.10 (m, 1H), 3.37-3.72 (m, 2H), 3.76-3.99 (m, 2H), 4.00-4.15 (m, 3H), 4.62-4.86 (m, 1H), 7.01-7.22 (m, 4H), 7.28-7.45 (m, 5H); MS m/z 431 (M+H)$^+$, 429 (M–H)$^-$.

Example 21

R06039-433

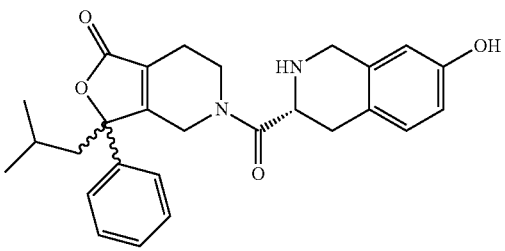

Chemical Formula: $C_{27}H_{30}N_2O_4$
Molecular Weight: 446.54

5-((R)-7-Hydroxy-1,2,3,4-tetrahydroisoquinoline-3-carbonyl)-3-isobutyl-3-phenyl-4,5,6,7-tetrahydrofuro[3,4-c]pyridin-1(3H)-one. To a solution of (R)-2-(tert-butoxycarbonyl)-7-hydroxy-1,2,3,4-tetrahydroisoquinoline-3-carboxylic acid (102 mg, 0.369 mmol), 3-isobutyl-3-phenyl-4,5,6,7-tetrahydrofuro[3,4-c]pyridin-1(3H)-one (50 mg, 0.184 mmol), and N,N'-diisopropylethylamine (112 mg, 0.870 mmol) in THF (5 mL) was added BOP reagent (144 mg, 0.326 mmol) and the mixture was stirred at room temperature for 16 hours. The reaction mixture was concentrated to dryness and the crude reaction mixture was concentrated and purified by column chromatography (12 g, SiO$_2$, 0 to 30% ethyl acetate in hexanes). The purified fractions were re-dissolved in dichloromethane (5 mL), cooled to 0° C. and stirred with TFA (1 mL) for 5 hours at room temperature. The reaction mixture was concentrated to dryness, re-dissolved in dichloromethane (20 mL), washed with sat. NaHCO$_3$ solution (5 mL), brine (5 mL), dried (MgSO$_4$), and concentrated to provide 5-((R)-7-hydroxy-1,2,3,4-tetrahydroisoquinoline-3-carbonyl)-3-isobutyl-3-phenyl-4,5,6,7-tetrahydrofuro[3,4-c]pyridin-1(3H)-one (55 mg, 67%) as a mixture of diastereoisomers in form of white solid: $^1$H NMR (300 MHz, CHLOROFORM-d) δ ppm 0.81-1.01 (m, 6H), 1.58-1.88 (m, 2H), 2.25-2.54 (m, 5H), 2.65-2.97 (m, 2H), 3.52 (d, J=6.40 Hz, 1H), 3.75-3.95 (m, 2H), 3.98-4.11 (m, 3H), 4.56-4.86 (m, 1H), 6.51 (s, 1H), 6.59-6.73 (m, 1H), 6.95 (t, J=8.48 Hz, 1H), 7.28-7.45 (m, 5H); MS m/z 447 (M+H)⁺.

Hz, 1H), 3.73 (dt, J=13.85, 4.94 Hz, 1H), 3.89-4.05 (m, 1H), 4.72 (d, J=19.59 Hz, 1H), 7.28-7.47 (m, 5H); MS m/z 397 (M+H)⁺, 395 (M−H)⁻.

Example 22

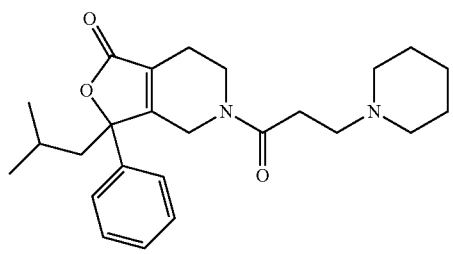

R06039-434

Chemical Formula: $C_{25}H_{34}N_2O_3$
Molecular Weight: 410.55

3-isobutyl-3-phenyl-5-(3-(piperidin-1-yl)propanoyl)-4,5,6,7-tetrahydrofuro[3,4-c]pyridin-1(3H)-one. The procedure described for R06039-421 was employed to convert 3-(piperidinyl)propanoic acid (58 mg, 0.369 mmol) to 3-isobutyl-3-phenyl-5-(3-(piperidin-1-yl)propanoyl)-4,5,6,7-tetrahydrofuro[3,4-c]pyridin-1(3H)-one (35 mg, 46%): ¹H NMR (300 MHz, CHLOROFORM-d) δ ppm 0.82-1.00 (m, 6H), 1.44 (m, J=5.30 Hz, 1H), 1.53-1.72 (m, 6H), 1.79 (dd, J=14.51, 7.35 Hz, 1H), 2.31 (dd, J=14.51, 4.71 Hz, 1H), 2.37-2.52 (m, 6H), 2.55-2.70 (m, 4H), 3.30-3.44 (m, 1H), 3.73 (dt, J=13.94, 4.90 Hz, 1H), 3.96 (d, J=19.59 Hz, 1H), 4.72 (d, J=19.59 Hz, 1H), 7.29-7.47 (m, 5H); MS m/z 411 (M+H)⁺, 409 (M−H)⁻.

Example 23

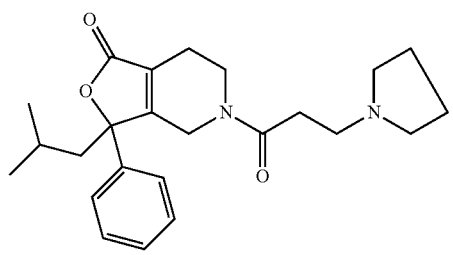

R06039-448

Chemical Formula: $C_{24}H_{32}N_2O_3$
Molecular Weight: 396.52

3-Isobutyl-3-phenyl-5-(3-(pyrrolidin-1-yl)propanoyl)-4,5,6,7-tetrahydrofuro[3,4-c]pyridin-1(3H)-one. The procedure described for R06039-421 was employed to convert 3-(pyrrolidin-1-yl)propanoic acid ¹ (53 mg, 0.368 mmol) to 3-isobutyl-3-phenyl-5-(3-(pyrrolidin-1-yl)propanoyl)-4,5,6,7-tetrahydrofuro[3,4-c]pyridin-1(3H)-one (10 mg, 15%): ¹H NMR (300 MHz, CHLOROFORM-d) δ ppm 0.81-1.00 (m, 6H), 1.59-1.73 (m, 1H), 1.74-1.88 (m, 4H), 2.31 (dd, J=14.51, 4.71 Hz, 2H), 2.42 (d, J=1.88 Hz, 2H), 2.47-2.59 (m, 4H), 2.59-2.70 (m, 2H), 2.70-2.89 (m, 2H), 3.37 (dt, J=13.37, 6.50

Example 24

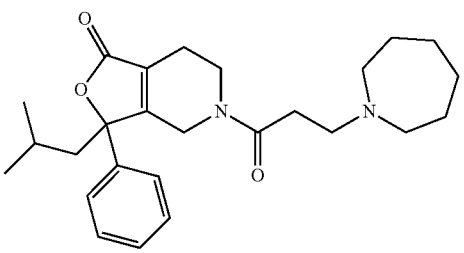

R06039-478

Chemical Formula: $C_{26}H_{36}N_2O_3$
Molecular Weight: 424.58

3-Isobutyl-3-phenyl-5-(3-(azepane-1-yl)propanoyl)-4,5,6,7-tetrahydrofuro[3,4-c]pyridin-1(3H)-one. The procedure described for R06039-421 was employed to convert 3-(azepane-1-yl)propanoic acid ¹ (53 mg, 0.368 mmol) to 3-isobutyl-3-phenyl-5-(3-(azepane-1-yl)propanoyl)-4,5,6,7-tetrahydrofuro[3,4-c]pyridin-1(3H)-one (40 mg, 52%). The desired product was purified by column chromatography (12 g, SiO₂, 0 to 2.5% methanol in dichloromethane) and semi-preparative HPLC and characterized as the TFA salt: ¹H NMR (300 MHz, CHLOROFORM-d) δ ppm 0.80-0.89 (m, 3H), 0.94 (d, J=6.78 Hz, 3H), 1.56-2.05 (m, 11H), 2.10-2.51 (m, 2H), 3.01 (d, J=4.90 Hz, 4H), 3.27-3.76 (m, 5H), 4.01 (d, J=19.59 Hz, 2H), 4.57 (s, 1H), 7.30-7.49 (m, 5H), 11.33-11.59 (m, 1H); MS m/z 425 (M+H)⁺.

Example 25

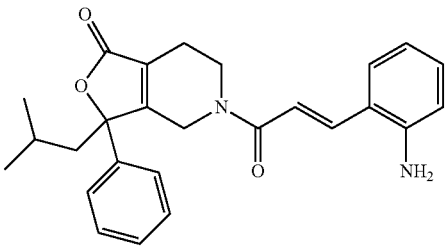

R06039-440

Chemical Formula: $C_{26}H_{28}N_2O_3$
Molecular Weight: 416.51

(E)-5-(3-(2-Aminophenyl)acryloyl)-3-isobutyl-3-phenyl-4,5,6,7-tetrahydrofuro[3,4-c]pyridin-1(3H)-one. A solution of (E)-3-isobutyl-5-(3-(2-nitrophenyl)acryloyl)-3-phenyl-4,5,6,7-tetrahydrofuro[3,4-c]pyridin-1(3H)-one (25 mg, 0.092 mmol) and tin(II)chloride hydrate (83 mg, 0.369 mmol) was heated in methanol (15 mL) for 2 hours. The reaction mixture was cooled to room temperature, concentrated to dryness, and re-dissolved in ethyl acetate (20 mL). The organic solution was washed with sat. NaHCO₃ solution (5 mL), brine (5 mL), dried (MgSO₄), and concentrated. Purification by column chromatography (4 g, SiO₂, 0 to 5% chloroform/methanol/ ammonium hydroxide 80:18:2 in dichloromethane) provided (E)-5-(3-(2-aminophenyl)acryloyl)-3-isobutyl-3-phenyl-4,5,6,7-tetrahydrofuro[3,4-c]pyridin-1(3H)-one as a white solid: ¹H NMR (300 MHz, CHLOROFORM-d) δ ppm 0.83-1.01 (m, 6H), 1.62-1.75 (m, 1H), 1.84 (dd, J=14.69, 7.16 Hz, 1H), 2.35 (dd, J=14.69, 4.52 Hz, 1H), 2.43-2.55 (m, 2H), 3.51 (m, J=5.70 Hz, 1H), 3.82-4.00 (m, 3H), 4.09 (d, J=19.59 Hz, 1H), 4.84 (d, J=19.21 Hz, 1H), 6.66-6.86 (m, 3H), 7.18 (t, J=7.54 Hz, 1H), 7.29-7.48 (m, 6H), 7.83 (d, J=15.07 Hz, 1H); MS m/z 417 (M+H)⁺, 439 (M+23)⁺, 415 (M−H)⁻.

Example 26

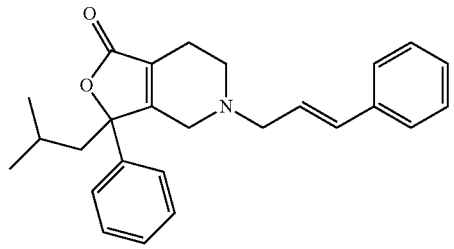

R06039-441

Chemical Formula: C₂₆H₂₉NO₂
Molecular Weight: 387.51

5-Cinnamoyl-3-isobutyl-3-phenyl-4,5,6,7-tetrahydrofuro[3,4-c]pyridin-1(3H)-one. To a solution of 3-isobutyl-3-phenyl-4,5,6,7-tetrahydrofuro[3,4-c]pyridin-1(3H)-one (50 mg, 0.184 mmol) in THF (5 mL) was added trans-cinnamaldehyde (49 mg, 0.369 mmol) and the reaction mixture stirred at room temperature for 1 hour. Sodium triacetoxyborohydride (117 mg, 0.553 mmol) was added and the reaction mixture stirred at room temperature for additional 2 hours. Ethyl acetate (10 mL) was added and the organic solution washed with sat. NaHCO₃ (10 mL), brine (10 mL), dried (MgSO₄), and concentrated. The residue was purified by column chromatography (12 g, SiO₂, 0 to 20% ethyl acetate in hexanes) to provide 5-cinnamoyl-3-isobutyl-3-phenyl-4,5,6,7-tetrahydrofuro[3,4-c]pyridin-1(3H)-one (45 mg, 63%) as a white solid: ¹H NMR (300 MHz, CHLOROFORM-d) δ ppm 0.73-1.05 (m, 6H), 1.54-1.84 (m, 2H), 2.20-2.48 (m, 3H), 2.52-2.66 (m, 1H), 2.73-2.89 (m, 1H), 2.99-3.14 (m, 1H), 3.19-3.37 (m, 2H), 3.43 (d, J=17.71 Hz, 1H), 6.23 (dt, J=15.82, 6.59 Hz, 1H), 6.44-6.57 (m, 1H), 7.20-7.46 (m, 10H); MS m/z 388 (M+H)⁺, 410 (M+23)⁺, 386 (M−H)⁻.

Example 27

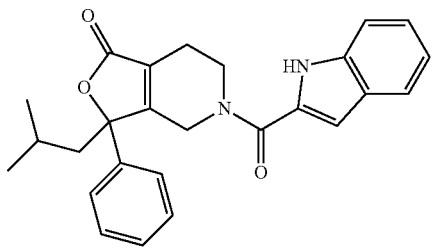

R06039-444

Chemical Formula: C₂₆H₂₉N₂O₃
Molecular Weight: 414.50

5-(1H-Indole-2-carbonyl)-3-isobutyl-3-phenyl-4,5,6,7-tetrahydrofuro[3,4-c]pyridin-1(3H)-one. The procedure described for R06039-421 was employed to convert 1H-indole-2-carboxylic acid (30 mg, 0.184 mmol) to 5-(1H-indole-2-carbonyl)-3-isobutyl-3-phenyl-4,5,6,7-tetrahydrofuro[3,4-c]pyridin-1(3H)-one (26 mg, 35%): ¹H NMR (300 MHz, CHLOROFORM-d) δ ppm 0.79-1.02 (m, 6H), 1.62-1.77 (m, 1H), 1.85 (dd, J=14.51, 7.35 Hz, 1H), 2.35 (dd, J=14.69, 4.52 Hz, 1H), 2.46-2.71 (m, 2H), 3.73-3.89 (m, 1H), 4.19-4.43 (m, 2H), 4.82 (d, J=19.59 Hz, 1H), 6.76 (br. s., 1H), 7.10-7.22 (m, 1H), 7.27-7.48 (m, 7H), 7.68 (d, J=7.91 Hz, 1H), 9.10 (br. s., 1H); MS m/z 415 (M+H)⁺, 437 (M+23)⁺, 413 (M−H)⁻.

Example 28

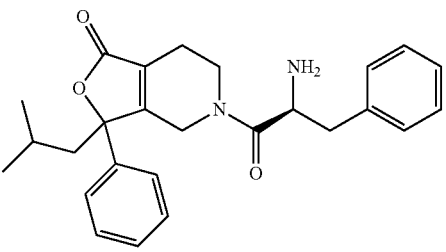

R06039-445

Chemical Formula: C₂₆H₃₀N₂O₃
Molecular Weight: 418.53

5-((S)-2-Amino-3-phenylpropanoyl)-3-isobutyl-3-phenyl-4,5,6,7-tetrahydrofuro[3,4-c]pyridin-1(3H)-one. The procedure described for R06039-432 was employed to convert (S)-2-(((9H-fluoren-9-yl)methoxy)carbonylamino)-3-phenylpropanoic acid (30 mg, 0.184 mmol) to 5-((S)-2-amino-3-phenylpropanoyl)-3-isobutyl-3-phenyl-4,5,6,7-tetrahydrofuro[3,4-c]pyridin-1(3H)-one. The desired product was purified by column chromatography (4 g, SiO₂, 0 to 10% chloroform/methanol/ammonium hydroxide 80:18:2 in dichloromethane) and isolated as a white solid (38 mg, 47%): ¹H NMR (300 MHz, CHLOROFORM-d) δ ppm 0.77-1.01 (m, 6H), 1.59-1.87 (m, 2H), 1.89-2.23 (m, 1H), 2.30 (dd, J=14.51, 4.71 Hz, 1H), 2.68-3.05 (m, 4H), 3.15-3.63 (m, 3H), 3.83-4.00 (m, 2H), 4.68 (dd, J=19.59, 6.40 Hz, 1H), 6.93-7.46 (m, 10H); MS m/z 419 (M+H)⁺, 441 (M+23)⁺, 417 (M−H)⁻.

Example 29

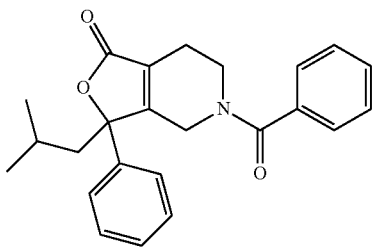

R06039-446

Chemical Formula: C₂₄H₂₅NO₃
Molecular Weight: 375.46

5-Benzoyl-3-isobutyl-3-phenyl-4,5,6,7-tetrahydrofuro[3,4-c]pyridin-1(3H)-one. The procedure described for R06039-427 was employed to convert benzoyl chloride (35 mg, 0.184 mmol) to 5-benzoyl-3-isobutyl-3-phenyl-4,5,6,7-tetrahydrofuro[3,4-c]pyridin-1(3H)-one (38 mg, 55%): $^1$H NMR (300 MHz, CHLOROFORM-d) δ ppm 0.78-1.06 (m, 6H), 1.62-1.96 (m, 2H)' 2.27-2.59 (m, 3H), 3.20-3.45 (m, 1H), 3.54-3.81 (m, 1H), 4.10 (d, J=19.97 Hz, 1H), 4.67-4.97 (m, 1H), 7.30-7.56 (m, 10H); MS m/z 376 (M+H)$^+$, 398 (M+23)$^+$, 374 (M−H)$^−$.

Example 30

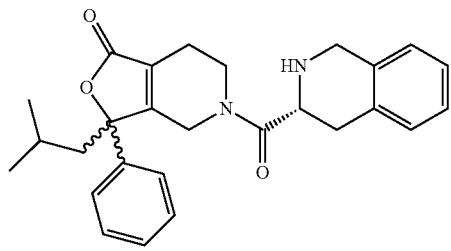

R06039-447

Chemical Formula: $C_{27}H_{30}N_2O_3$
Molecular Weight: 430.54

3-Isobutyl-3-phenyl-5-((R)-1,2,3,4-tetrahydroisoquinoline-3-carbonyl)-4,5,6,7-tetrahydrofuro[3,4-c]pyridin-1(3H)-one. The procedure described for R06039-433 was employed to convert (R)-2-(tert-butoxycarbonyl)-1,2,3,4-tetrahydroisoquinoline-3-carboxylic acid (102 mg, 0.368 mmol) to 3-isobutyl-3-phenyl-5-((R)-1,2,3,4-tetrahydroisoquinoline-3-carbonyl)-4,5,6,7-tetrahydrofuro[3,4-c]pyridin-1(3H)-one (15 mg, 19%): $^1$H NMR (300 MHz, CHLOROFORM-d) δ ppm 0.81-1.03 (m, 6H), 1.58-1.74 (m, 1H), 1.80 (dd, J=14.69, 7.16 Hz, 1H), 1.93-2.18 (m, 1H), 2.26-2.64 (m, 3H), 2.71-2.85 (m, 1H), 2.98 (dd, J=16.58, 11.30 Hz, 1H), 3.36-3.76 (m, 1H), 3.78-4.07 (m, 3H), 4.08-4.17 (m, 2H), 4.79 (d, J=19.59 Hz, 1H), 6.99-7.23 (m, 4H), 7.29-7.46 (m, 5H); MS m/z 431 (M+H)$^+$, 429 (M−H)$^−$.

Example 31

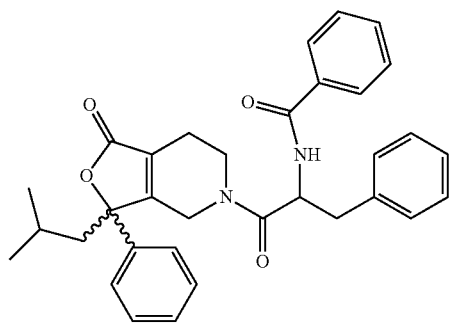

R06039-449

Chemical Formula: $C_{33}H_{34}N_2O_4$
Molecular Weight: 522.63

N-((2S)-1-(3-Isobutyl-1-oxo-3-phenyl-6,7-dihydrofuro[3,4-c]pyridin-5(1H,3H,4H)-yl)-1-oxo-3-phenylpropan-2-yl)benzamide. The procedure described for R06039-427 was employed to convert benzoyl chloride (6 mg, 0.041 mmol) to 5-((S)-2-amino-3-phenylpropanoyl)-3-isobutyl-3-phenyl-4,5,6,7-tetrahydrofuro[3,4-c]pyridin-1(3H)-one (16 mg, 0.037 mmol) to provide N-((2S)-1-(3-isobutyl-1-oxo-3-phenyl-6,7-dihydrofuro[3,4-c]pyridin-5 (1H,3H,4H)-yl)-1-oxo-3-phenylpropan-2-yl)benzamide. The desired product was purified by column chromatography (4 g, SiO$_2$, 0 to 100% dichloromethane/diethylether in hexanes) and isolated as a colorless oil (13 mg, 69%): $^1$H NMR (300 MHz, CHLOROFORM-d) δ ppm 0.76-0.95 (m, 6H), 1.46-1.92 (m, 4H), 2.06-2.39 (m, 2H), 2.99-3.37 (m, 2H), 3.40-3.62 (m, 1H), 3.82-4.07 (m, 1H), 4.60 (d, J=19.59 Hz, 1H), 5.15-5.30 (m, 1H), 5.31-5.50 (m, 1H), 6.94-7.57 (m, 13H), 7.70-7.85 (m, 2H); MS m/z 523 (M+H)$^+$, 521 (M−H)$^−$.

Example 32

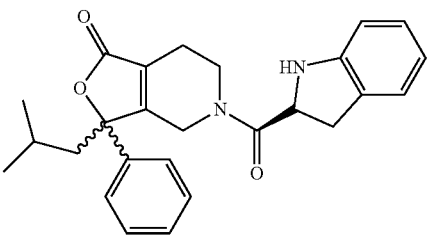

R06039-450 and

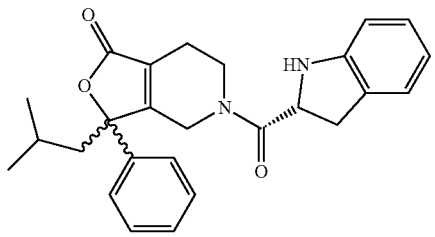

R06039-451

Chemical Formula: $C_{26}H_{28}N_2O_3$
Molecular Weight: 416.51

5-(Indoline-2-carbonyl)-3-isobutyl-3-phenyl-4,5,6,7-tetrahydrofuro[3,4-c]pyridin-1(3H)-one (Mixture of Diastereoisomers). The procedure described for 806039-421 was employed to convert indoline-2-carboxylic acid (60 mg, 0.368 mmol) to 5-(indoline-2-carbonyl)-3-isobutyl-3-phenyl-4,5,6,7-tetrahydrofuro[3,4-c]pyridin-1(3H)-one. The desired product was purified by column chromatography (12 g, SiO$_2$, 0 to 2.5% methanol in dichloromethane) and isolated as a mixture of diastereomers: Diastereomers A (upper TLC spot), colorless oil (28 mg, 369%): $^1$H NMR (300 MHz, CHLOROFORM-d) δ ppm 0.76-1.05 (m, 6H), 1.60-1.87 (m, 2H), 2.23-2.60 (m, 3H), 3.09 (dd, J=15.64, 5.09 Hz, 1H), 3.44-3.61 (m, 2H), 3.63-3.77 (m, 1H), 4.04 (d, J=19.59 Hz, 1H), 4.24-4.46 (m, 1H), 4.49-4.77 (m, 2H), 6.67-6.86 (m, 2H), 6.97-7.14 (m, 2H), 7.28-7.47 (m, 5H); MS m/z 417 (M+H)$^+$, 439 (M+23)$^+$, 415 (M−H)$^−$. Diastereomers B (lower TLC spot), colorless oil (28 mg, 36%): $^1$H NMR (300 MHz, CHLOROFORM-d) δ ppm 0.80-1.01 (m, 6H), 1.48-1.85 (m, 2H), 2.25-2.56 (m, 2H), 3.15 (dd, J=15.64, 5.46 Hz, 1H), 3.31-3.62 (m, 2H), 3.74-3.87 (m, 1H), 3.94-4.20 (m, 2H), 4.35-4.46 (m, 1H), 4.55-4.77 (m, 2H), 6.70-6.83 (m, 2H), 7.07 (d, J=5.27 Hz, 2H), 7.29-7.49 (m, 5H); MS m/z 417 (M+H)⁺, 439 (M+23)⁺, 415 (M−H)⁻.

Example 33

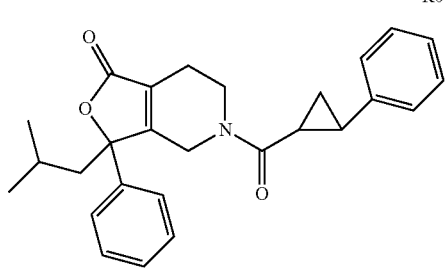

R06039-452

Chemical Formula: C₂₈H₂₇NO₃
Molecular Weight: 425.52 trans-3-Isobutyl-3-phenyl-5-(2-phenylcyclopropanecarbonyl)-4,5,6,7-tetrahydrofuro[3,4-c]pyridin-1(3H)-one. The procedure described for R06039-421 was employed to convert trans-2-phenylcyclopropyl carboxylic acid (60 mg, 0.368 mmol) to trans-3-isobutyl-3-phenyl-5-(2-phenylcyclopropanecarbonyl)-4,5,6,7-tetrahydrofuro[3,4-c]pyridin-1(3H)-one (29.3 mg, 38%): ¹H NMR (300 MHz, CHLOROFORM-d) δ ppm 0.83-0.99 (m, 6H), 1.28-1.38 (m, 2H), 1.59-1.74 (m, 2H), 1.80 (dd, J=14.51, 7.35 Hz, 1H), 1.93-2.03 (m, 1H), 2.25-2.56 (m, 3H), 3.37-3.59 (m, 1H), 3.80-4.04 (m, 1H), 3.88-3.89 (m, 1H), 4.74 (dd, J=19.59, 14.69 Hz, 1H), 7.11 (t, J=6.78 Hz, 2H), 7.17-7.43 (m, 8H); MS m/z 417 (M+H)⁺, 439 (M+23)⁺, 415 (M−H)⁻.

Example 34

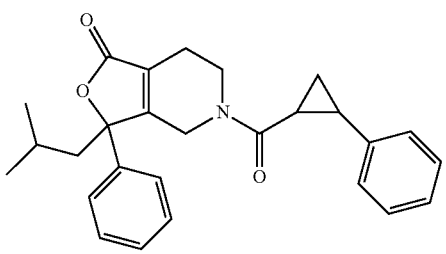

R06039-453

Chemical Formula: C₂₈H₂₇NO₃
Molecular Weight: 425.52 cis-3-Isobutyl-3-phenyl-5-(2-phenylcyclopropanecarbonyl)-4,5,6,7-tetrahydrofuro[3,4-c]pyridin-1(3H)-one. The procedure described for R06039-421 was employed to convert cis-2-phenylcyclopropyl carboxylic acid (60 mg, 0.368 mmol) to cis-3-isobutyl-3-phenyl-5-(2-phenylcyclopropanecarbonyl)-4,5,6,7-tetrahydrofuro[3,4-c]pyridin-1(3H)-one (25 mg, 33%): ¹H NMR (300 MHz, CHLOROFORM-d) δ ppm 0.77-0.93 (m, 6H), 1.18-1.38 (m, 2H), 1.48-1.80 (m, 3H), 1.88 (dt, J=12.62, 6.12 Hz, 1H), 2.11-2.30 (m, 2H), 2.46-2.58 (m, 1H), 3.07 (ddd, J=13.85, 9.51, 4.14 Hz, 1H), 3.43-3.55 (m, 1H), 4.00-4.14 (m, 1H), 4.70 (d, J=19.59 Hz, 1H), 7.03-7.43 (m, 10H); MS m/z 417 (M+H)⁺, 439 (M+23)⁺, 415 (M−H)⁻.

Example 35

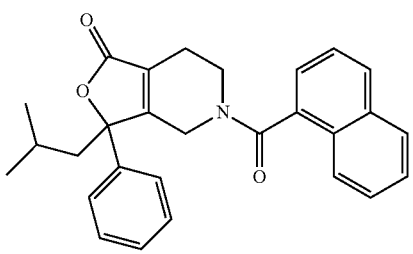

R06039-454

Chemical Formula: C₂₈H₂₇NO₃
Molecular Weight: 425.52

5-(1-Naphthoyl)-3-isobutyl-3-phenyl-4,5,6,7-tetrahydrofuro[3,4-c]pyridin-1(3H)-one. The procedure described for R06039-421 was employed to convert 1-naphthoic acid (63 mg, 0.368 mmol) to 5-(1-naphthoyl)-3-isobutyl-3-phenyl-4,5,6,7-tetrahydrofuro[3,4-c]pyridin-1(3H)-one (15.6 mg, 20%): ¹H NMR (300 MHz, CHLOROFORM-d) δ ppm 0.80-1.07 (m, 6H), 1.65-1.82 (m, 1H), 1.84-2.01 (m, 1H), 2.23 (br. s., 1H), 2.36-2.53 (m, 1H), 3.04-3.30 (m, 1H), 3.43 (td, J=8.95, 4.33 Hz, 1H), 3.63-4.12 (m, 1H), 4.25 (t, J=19.78 Hz, 1H), 4.96-5.27 (m, 1H), 7.31-7.59 (m, 8H), 7.62-7.79 (m, 1H), 7.81-7.98 (m, 3H); MS m/z 426 (M+H)⁺, 448 (M+23)⁺, 424 (M−H)⁻.

Example 36

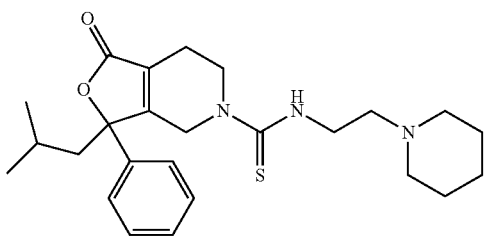

R06039-237

Chemical Formula: C₂₅H₃₅N₃O₂S
Molecular Weight: 441.63

3-isobutyl-1-oxo-3-phenyl-N-(2-(piperidin-1-yl)ethyl)-3,4,6,7-tetrahydrofuro[3,4-c]pyridine-5(1H)-carbothioamide. A mixture of 3-phenyl-3-isobutyl-4,5,6,7-tetrahydrofuro[3,4-c]pyridin-1(3H)-one (50 mg, 0.18 mmol) and 1-(isothiocyanatoethyl)piperidine (45.7 mg, 0.28 mmol) in dichloromethane (5 mL) was stirred at room temperature for 1 h. The solvent was removed and the resulting residue was purified on silica to give the desired product (52 mg, 64.0%). ¹H NMR (300 Hz, CDCl₃) δ 0.87 (t, J=6.0, 3H), 0.96 (t, d=6.0, 3H), 1.40-1.63 (m, 6H), 1.63-1.75 (m, 1H), 1.78-1.90 (m, 1H), 2.30-2.60 (m, 10H), 2.58-2.70 (m, 3H), 3.83-3.95 (m, 1H), 4.26 (d, J=18.0, 1H), 5.17 (d, J=18.0, 1H), 7.02 (br s, 1H), 7.26-7.40 (m, 5H).

Example 37

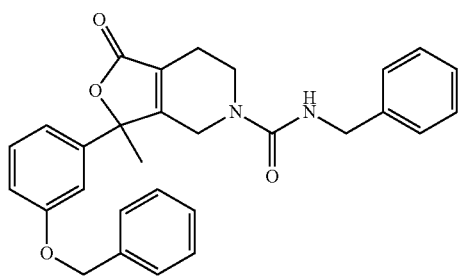

R06039-244

Chemical Formula: C29H28N2O4
Molecular Weight: 468.54

N-benzyl-3-(3-(benzyloxy)phenyl)-3-methyl-1-oxo-3,4,6,7-tetrahydrofuro[3,4-c]pyridine-5(1H)-carboxamide. A mixture of 3-(3-benzyloxyphenyl)-3-methyl-4,5,6,7-tetrahydrofuro[3,4-c]pyridin-1(3H)-one (50 mg, 0.15 mmol) and benzyl isocyanate (27 μL, 0.22 mmol) in dichloromethane (5 mL) was stirred at room temperature for 1 h. The solvent was removed and the resulting residue was purified on silica to give the desired product (43 mg, 61.6%). $^1$H NMR (300 Hz, CDCl$_3$) δ 1.84 (s, 3H), 2.38 (br s, 2H), 3.26-3.32 (m, 1H), 3.51-3.58 (m, 1H), 3.79 (d, J=18.0, 1H), 4.37-4.30 (m, 3H), 4.94 (t, J=6.0, 1H), 5.04 (s, 2H), 6.87-6.94 (m, 3H), 7.24-7.39 (m, 11H).

Example 38

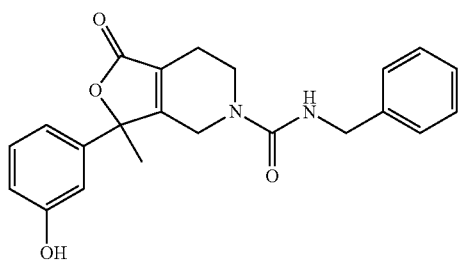

R06039-243

Chemical Formula: C22H22N2O4
Molecular Weight: 378.42

N-benzyl-3-(3-hydroxyphenyl)-3-methyl-1-oxo-3,4,6,7-tetrahydrofuro[3,4-c]pyridine-5(1H)-carboxamide. A mixture of 3-(3-hydroxyphenyl)-3-methyl-4,5,6,7-tetrahydrofuro[3,4-c]pyridin-1(3H)-one (75 mg, 0.31 mmol) and benzyl isocyanate (48 μL, 0.40 mmol) in dichloromethane (5 mL) was stirred at room temperature for 1 h. The solvent was removed and the resulting residue was purified on silica to give the desired product (68 mg, 58.8%). $^1$H NMR (300 Hz, CDCl$_3$) δ 1.82 (s, 3H), 2.39 (br s, 2H), 3.30-3.40 (m, 1H), 3.42-3.55 (m, 1H), 3.94 (d, J=18.0, 1H), 4.25-4.40 (m, 3H), 4.97 (t, J=6.0, 1H), 6.77-6.84 (m, 2H), 7.15-7.38 (m, 7H).

Example 39

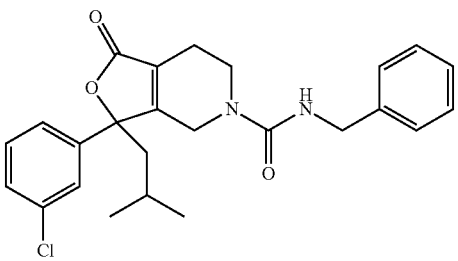

R06039-242

Chemical Formula: C25H27ClN2O3
Molecular Weight: 438.95

N-benzyl-3-(3-chlorophenyl)-3-isobutyl-1-oxo-3,4,6,7-tetrahydrofuro[3,4-c]pyridine-5(1H)-carboxamide. A mixture of 3-(3-chlorophenyl)-3-isobutyl-4,5,6,7-tetrahydrofuro[3,4-c]pyridin-1(3H)-one (70 mg, 0.23 mmol) and benzyl isocyanate (42 μL, 0.34 mmol) in dichloromethane (5 mL) was stirred at room temperature for 1 h. The solvent was removed and the resulting residue was purified on silica to give the desired product (105 mg, 100%). $^1$H NMR (300 Hz, CDCl$_3$) δ 0.85 (d, J=6.0, 3H), 0.93 (d, J=6.0, 3H), 1.55-1.70 (m, 1H), 1.72-1.82 (m, 1H), 2.20-2.40 (m, 3H), 3.15-3.29 (m, 1H), 3.49-3.61 (m, 1H), 3.89 (d, J=18.0, 1H), 4.39 (d, J=3.0, 2H), 4.48 (d, J=18.0, 1H), 5.22 (t, J=6.0, 1H), 7.14-7.38 (m, 9H).

Example 40

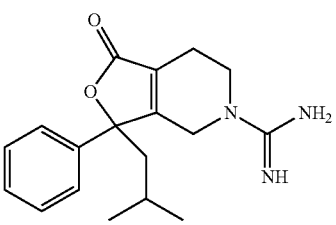

R06039-246

Chemical Formula: C18H23N3O2
Molecular Weight: 313.39

3-isobutyl-1-oxo-3-phenyl-3,4,6,7-tetrahydrofuro[3,4-c]pyridine-5(1H)-carboximidamide. A mixture of 3-phenyl-3-isobutyl-4,5,6,7-tetrahydrofuro[3,4-c]pyridin-1(3H)-one (170 mg, 0.60 mmol), 1,3-bis-tert-butoxycarbonyl-2-methyl-2-thiopseudourea (346 mg, 1.20 mmol), mercury (II) chloride (281 mg, 0.60 mmol) and triethylamine (0.2 mL, 1.20 mmol) in dimethylformamide (10 mL) was stirred at 50° C. for 20 h. The reaction was allowed to cool to room temperature and filtered. Saturated sodium bicarbonate solution (15 mL) was added to the filtrate and the mixture was extracted with ethyl acetate (3×50 mL). The combined organic layers were washed with water and brine, dried with MgSO$_4$ and concentrated to give the crude product. The material was used in the next step without further purification.

The above compound was dissolved in dichloromethane (5 mL) and cooled to 0° C. Trifluoroacetic acid (1 mL) was added. The reaction was allowed to stirred for 15 h. The solvent was then removed and resulting residue was recrystallized in ethyl acetate/petroleum ether to give the final product as the di-TFA salt (4.6 mg, 1.3% over both steps). $^1$H NMR (300 Hz, $CD_3OD$) δ 1.95-2.00 (m, 1H), 2.43-2.50 (m, 1H), 3.35-3.46 (m, 1H), 3.68-3.76 (m, 1H), 4.04-4.12 (m, 1H), 4.54-4.60 (m, 1H), 7.32-7.45 (m, 5H).

Example 41

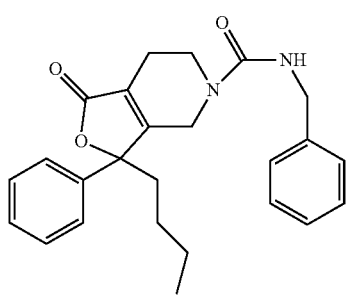

R06039-222

Chemical Formula: $C_{25}H_{28}N_2O_3$
Molecular Weight: 404.5

N-benzyl-3-butyl-1-oxo-3-phenyl-3,4,6,7-tetrahydrofuro[3,4-c]pyridine-5(1H)-carboxamide. Benzyl isocyanate (0.02 g, 0.14 mmol) was added to a solution of 3-phenyl-3-butyl-4,5,6,7-tetrahydrofuro[3,4-c]pyridin-1(3H)-one (0.025 g, 0.09 mmol prepared in a manner analogous to compound 2) in dichloromethane (5 mL) and was stirred at room temperature for 1 h. The solvent was removed and the resulting residue was purified on silica to give the desired product (0.018 g, 50%). $^1$H NMR (300 MHz, CHLOROFORM-d) δ ppm 0.79 (t, J=7.16 Hz, 3H), 1.06-1.33 (m, 4H), 1.83-1.97 (m, 1H), 2.14-2.43 (m, 3H), 3.18-3.31 (m, 1H), 3.36-3.51 (m, 1H), 3.85 (dt, J=18.84, 2.64 Hz, 1H), 4.26-4.39 (m, 3H), 4.90 (t, J=5.27 Hz, 1H), 7.11-7.36 (m, 10H).

Example 42

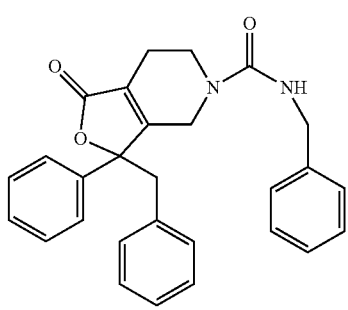

R06039-225

Chemical Formula: $C_{28}H_{26}N_2O_3$
Molecular Weight: 438.52

N,3-dibenzyl-1-oxo-3-phenyl-3,4,6,7-tetrahydrofuro[3,4-c]pyridine-5(1H)-carboxamide. Benzyl isocyanate (0.02 6 g, 0.2 mmol) was added to a solution of 3-phenyl-3-benzyl-4,5,6,7-tetrahydrofuro[3,4-c]pyridin-1(3H)-one (0.05 g, 0.16 mmol prepared in a manner analogous to compound 2) in dichloromethane (5 mL) and was stirred at room temperature for 1 h. The solvent was removed and the resulting residue was purified on silica to give the desired product (0.036 g, 50%). $^1$H NMR (300 MHz, CHLOROFORM-d) δ ppm 1.93-2.08 (m, 1H), 2.11-2.23 (m, 1H), 3.11-3.35 (m, 2H), 3.39-3.49 (m, 1H), 3.52-3.62 (m, 1H), 3.97-4.08 (m, 1H), 4.42 (dd, J=5.27, 2.64 Hz, 2H), 4.59 (dt, J=19.12, 2.12 Hz, 1H), 4.90 (t, J=5.46 Hz, 1H), 7.15-7.47 (m, 15H).

Example 43

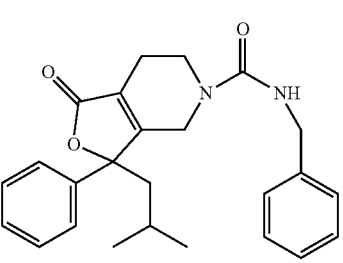

R06039-226

Chemical Formula: $C_{25}H_{28}N_2O_3$
Molecular Weight: 404.50

N-benzyl-3-isobutyl-1-oxo-3-phenyl-3,4,6,7-tetrahydrofuro[3,4-c]pyridine-5(1H)-carboxamide. Benzyl isocyanate (0.02 9 g, 0.22 mmol) was added to a solution of 3-phenyl-3-isobutyl-4,5,6,7-tetrahydrofuro[3,4-c]pyridin-1(3H)-one (0.05 g, 0.184 mmol prepared in a manner analogous to compound 2) in dichloromethane (5 mL) and was stirred at room temperature for 1 h. The solvent was removed and the resulting residue was purified on silica to give the desired product (0.051 g, 68%). $^1$H NMR (300 MHz, CHLOROFORM-d) δ ppm 0.85 (d, J=6.40 Hz, 3H), 0.89-0.98 (m, 3H), 1.65 (ddd, J=13.56, 6.78, 4.90 Hz, 1H), 1.73-1.87 (m, 1H), 2.24-2.40 (m, 3H), 3.27 (ddd, J=13.56, 7.35, 5.09 Hz, 1H), 3.54 (dt, J=13.66, 5.23 Hz, 1H), 3.92 (dt, J=18.84, 2.64 Hz, 1H), 4.40 (d, J=5.65 Hz, 2H), 4.49 (dt, J=19.12, 2.12 Hz, 1H), 5.00 (t, J=5.46 Hz, 1H), 7.21-7.42 (m, 10H).

Example 44

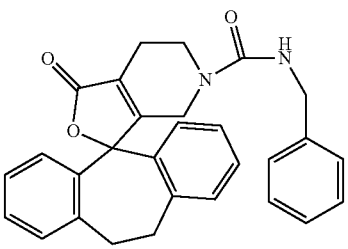

R06039-221

Chemical Formula: $C_{29}H_{26}N_2O_3$
Molecular Weight: 450.53

N-benzyl-1'-oxo-1',4',6',7',10,11-hexahydro-5'H-spiro[dibenzo[a,d][7]annulene-5,3'-furo[3,4-c]pyridine]-5'-carboxamide. Benzyl isocyanate (0.03 g, 0.21 mmol) was added to a solution of 1',4',6',7',10,11-hexahydro-5'H-spiro[dibenzo[a,d][7]annulene-5,3'-furo[3,4-c]pyridin-1(3H)-one (0.053 g, 0.14 mmol prepared in a manner analogous to compound 2) in dichloromethane (5 mL) and was stirred at room temperature for 1 h. The solvent was removed and the resulting residue was purified on silica to give the desired product (0.048 g, 76%). $^1$H NMR (300 MHz, CHLOROFORM-d) δ ppm 2.49 (tt, J=5.32, 2.59 Hz, 2H), 3.05-3.19 (m, 4H), 3.44 (t, J=5.65 Hz, 2H), 4.08-4.12 (m, 2H), 4.34 (d, J=5.27 Hz, 2H), 4.85 (t, J=5.27 Hz, 1H), 7.12-7.34 (m, 13H).

Example 45

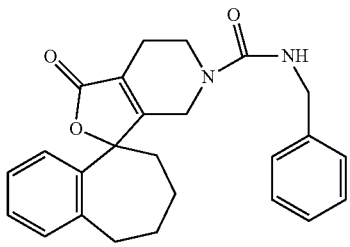

Chemical Formula: $C_{25}H_{26}N_2O_3$
Molecular Weight: 402.49

N-benzyl-1'-oxo-6,6',7,7',8,9-hexahydro-1'H-spiro[benzo[7]annulene-5,3'-furo[3,4-c]pyridine]-5'(4'H)-carboxamide. Benzyl isocyanate (0.033 g, 0.25 mmol) was added to a solution of 6',7,7',8,9-hexahydro-1'H-spiro[benzo[7]annulene-5,3'-furo[3,4-c]pyridine]-1(3H)-one (0.068 g, 0.25 mmol prepared in a manner analogous to compound 2) in dichloromethane (5 mL) and was stirred at room temperature for 1 h. The solvent was removed and the resulting residue was purified on silica to give the desired product (0.071 g, 71%). $^1$H NMR (300 MHz, CHLOROFORM-d) δ ppm 1.62-1.77 (m, 1H), 1.79-2.11 (m, 4H), 2.12-2.27 (m, 1H), 2.35-2.44 (m, 2H), 2.78-2.92 (m, 1H), 2.99-3.12 (m, 1H), 3.53 (td, J=5.56, 2.07 Hz, 2H), 4.18-4.32 (m, 1H), 4.33-4.45 (m, 3H), 5.14 (t, J=5.46 Hz, 1H), 6.91-6.98 (m, 1H), 7.07-7.38 (m, 8H).

Example 46

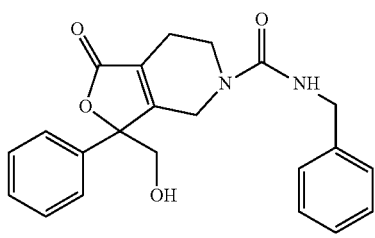

Chemical Formula: $C_{22}H_{22}N_2O_4$
Molecular Weight: 378.42

N-benzyl-3-(hydroxymethyl)-1-oxo-3-phenyl-3,4,6,7-tetrahydrofuro[3,4-c]pyridine-5(1H)-carboxamide. Benzyl isocyanate (0.069 g, 0.52 mmol) was added to a solution of 3-phenyl-3-hydroxymethyl-4,5,6,7-tetrahydrofuro[3,4-c]pyridin-1(3H)-one (0.128 g, 0.52 mmol prepared in a manner analogous to compound 2) in dichloromethane (10 mL) and was stirred at room temperature for 1 h. The solvent was removed and the resulting residue was purified on silica to give the desired product (0.101 g, 51%). $^1$H NMR (300 MHz, CHLOROFORM-d) δ ppm 2.18-2.47 (m, 2H), 3.19-3.31 (m, 1H), 3.63 (dt, J=13.75, 4.99 Hz, 1H), 3.94-4.07 (m, 3H), 4.07-4.18 (m, 1H), 4.35 (d, J=5.65 Hz, 2H), 4.47 (d, J=18.84 Hz, 1H), 5.50 (t, J=5.65 Hz, 1H), 7.15-7.25 (m, 4H), 7.27-7.42 (m, 6H).

Example 47

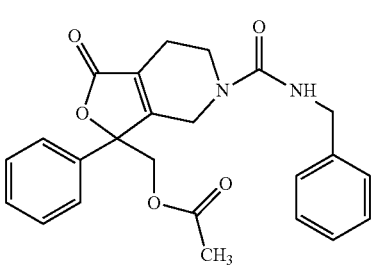

Chemical Formula: $C_{24}H_{24}N_2O_5$
Molecular Weight: 420.46

(5-(Benzylcarbamoyl)-1-oxo-3-phenyl-1,3,4,5,6,7-hexahydrofuro[3,4-c]pyridin-3-yl)methyl acetate. R06039-240 (0.050 g, 0.13 mmol) was dissolved in dichloromethane (5 mL) and $NEt_3$ (16 mg, 0.016 mmol), and cooled to 0° C. Acetyl chloride (13 mg, 0.16 mmol) was added to the reaction mixture, stirred at 0° C. for 30 min, and concentrated to dryness. The crude mixture was purified by column chromatography (4 g, $SiO_2$, 0 to 100% ethyl acetate in hexanes) to provide (5-(benzylcarbamoyl)-1-oxo-3-phenyl-1,3,4,5,6,7-hexahydrofuro[3,4-c]pyridin-3-yl)methyl acetate (0.031 g, 57%), $^1$H NMR (300 MHz, CHLOROFORM-d) δ ppm 2.00 (s, 3H), 2.42 (tt, J=4.85, 2.68 Hz, 2H), 3.33 (ddd, J=13.66, 6.50, 5.09 Hz, 1H), 3.58-3.69 (m, 1H), 4.01 (dt, J=18.84, 2.64 Hz, 1H), 4.35-4.45 (m, 3H), 4.50 (d, J=12.06 Hz, 1H), 4.85 (d, J=12.06 Hz, 1H), 4.94 (t, J=5.46 Hz, 1H), 7.23-7.45 (m, 10H).

Example 48

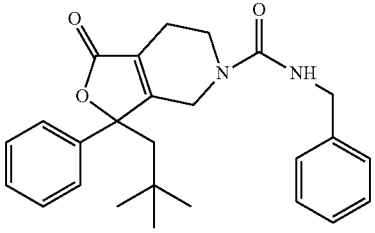

Chemical Formula: $C_{26}H_{42}N_2O_3$
Molecular Weight: 430.62

N-Benzyl-3-neopentyl-1-oxo-3-phenyl-3,4,6,7-tetrahydrofuro[3,4-c]pyridine-5(1H)-carboxamide. Benzyl isocyanate (0.02 g, 0.15 mmol) was added to a solution of 3-phenyl-3-neopentyl-4,5,6,7-tetrahydrofuro[3,4-c]pyridin-1(3H)-one (0.043 g, 0.15 mmol prepared in a manner analogous to compound 2) in dichloromethane (10 mL) and was stirred at room temperature for 1 h. The solvent was removed and the resulting residue was purified on silica to give the desired product (0.041 g, 63%). ¹H NMR (300 MHz, CHLOROFORM-d) δ ppm 0.87 (s, 9H), 1.88 (d, J=14.88 Hz, 1H), 2.28-2.43 (m, 2H), 2.38 (d, J=14.88 Hz, 1H), 3.16-3.28 (m, 1H), 3.53 (s, 1H), 3.96 (dt, J=19.03, 2.50 Hz, 1H), 4.42 (d, J=5.65 Hz, 2H), 4.59 (s, 1H), 4.88-4.99 (m, 1H), 7.20-7.41 (m, 10H).

Example 49

R06039-270

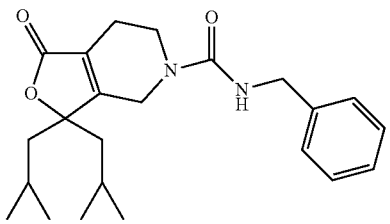

Chemical Formula: C₂₃H₃₈N₂O₃
Molecular Weight: 390.56

N-Benzyl-3,3-diisobutyl-1-oxo-3,4,6,7-tetrahydrofuro[3,4-c]pyridine-5 (1H)-carboxamide. Benzyl isocyanate (0.04 g, 0.3 mmol) was added to a solution of 3,3-diisobutyl-4,5,6,7-tetrahydrofuro[3,4-c]pyridin-1(3H)-one (0.075 g, 0.30 mmol prepared in a manner analogous to compound 2) in dichloromethane (10 mL) and was stirred at room temperature for 1 h. The solvent was removed and the resulting residue was purified on silica to give the desired product (0.042 g, 36%). ¹H NMR (300 MHz, CHLOROFORM-d) δ ppm 0.75-0.93 (m, 12H), 1.39-1.60 (m, 4H), 1.77-1.92 (m, 2H), 2.28-2.45 (m, 2H), 3.36-3.55 (m, 2H), 4.03-4.18 (m, 2H), 4.34-4.48 (m, 2H), 4.85-5.03 (m, 1H), 7.17-7.39 (m, 5H).

Example 50

R06039-286

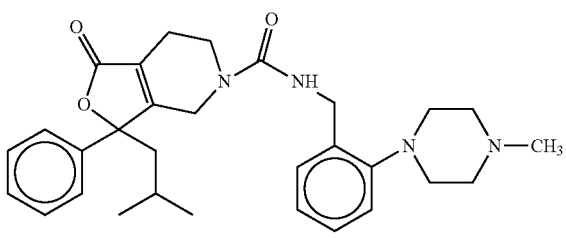

Chemical Formula: C₃₀H₅₀N₄O₃
Molecular Weight: 514.74

3-Isobutyl-N-(2-(4-methylpiperazin-1-yl)benzyl)-1-oxo-3-phenyl-3,4,6,7-tetrahydrofuro[3,4-c]pyridine-5(1H)-carboxamide. An analogous procedure to that described for R06039-275 was used to convert [2-(4-methylpiperazin-1-yl)phenyl]methanamine to 3-cyclohexyl-3-isobutyl-N-((2-(4-methylpiperazin-1-yl)cyclohexyl)methyl)-1-oxo-3,4,6,7-tetrahydrofuro[3,4-c]pyridine-5(1H)-carboxamide using triphosgene and triethylamine. ¹H NMR (300 MHz, CHLOROFORM-d) δ ppm 0.82-0.90 (m, 3H), 0.90-1.00 (m, 3H), 1.58-1.73 (m, 1H), 1.74-1.88 (m, 1H), 2.25-2.46 (m, 3H), 2.34 (s, 3H), 2.49-2.67 (m, 4H), 2.98 (t, J=4.90 Hz, 4H), 3.23-3.38 (m, 1H), 3.55 (dt, J=13.56, 5.09 Hz, 1H), 3.93 (dt, J=19.21, 2.64 Hz, 1H), 4.43-4.59 (m, 3H), 6.05 (t, J=5.27 Hz, 1H), 7.02-7.19 (m, 2H), 7.22-7.43 (m, 7H).

Example 51

R06039-202

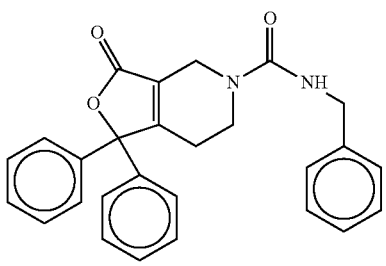

Chemical Formula: C₂₇H₄₂N₂O₃
Molecular Weight: 442.63

N-Benzyl-3-oxo-1,1-diphenyl-3,4,6,7-tetrahydrofuro[3,4-c]pyridine-5 (1H)-carboxamide. The title compound was synthesized in a manner analogous to R06039-222 except 3-diisopropylamidopyridine was coupled to benzophenone to provide intermediate 1,1-diphenylfuro[3,4-c]pyridin-3-one. 1,1-diphenylfuro[3,4-c]pyridin-3-one was reduced in a manner analogous to 3,3-diphenyl-4,5,6,7-tetrahydrofuro[3,4-c]pyridin-1(3H)-one (compound 2) to afford 1,1-diphenyl-4,5,6,7-tetrahydrofuro[3,4-c]pyridin-3-one. Benzyl isocyanate (0.023 g, 0.17 mmol) was then added to a solution of 1,1-diphenyl-4,5,6,7-tetrahydrofuro[3,4-c]pyridin-3-one (0.05 g, 0.17 mmol) in dichloromethane (10 mL) and was stirred at room temperature for 1 h. The solvent was removed and the resulting residue was purified on silica to give the desired product (0.038 g, 50%). ¹H NMR (300 MHz, CHLOROFORM-d) δ ppm 3.66-3.70 (dd, 2H, J=6 Hz), 4.10-4.15 (m, 2H), 4.34-4.42 (dd, 2H, J=6 Hz), 5.09 (t, 1H, J=6 Hz), 7.20-7.38 (m, 15H).

Example 52

R06039-211

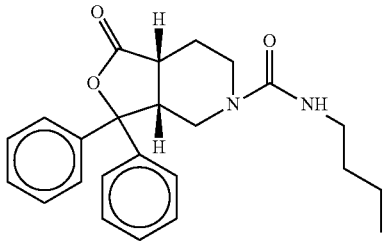

Chemical Formula: C₂₄H₄₀N₂O₃
Molecular Weight: 404.59

(cis 3a,7a)-N-Butyl-1-oxo-3,3-diphenylhexahydrofuro[3,4-c]pyridine-5 (1H)-carboxamide. 3,3-Diphenyl-4,5,6,7-tetrahydrofuro[3,4-c]pyridin-1(3H)-one (0.16 g, 0.55 mmol) in MeOH at 10° C. (20 mL) was treated with NaBH₄ (0.11 g, 3.0 mmol) and NiCl₂ hydrate (0.04 g, 0.03 mmol). The reaction mixture turned black and was allowed to come to room temperature over 2 h. The reaction was quenched with sat. NaHCO₃ (15 mL) and extracted with EtOAc (3×20 mL). The extracts were dried (MgSO₄), and concentrated under reduced pressure. The resulting oil was purified on silica (chloroform/MeOH, NH4OH, 80:18:2) to afford 0.67 mg (42%) of cis 1,1-diphenyl-hexahydrofuro[3,4-c]pyridin-3-one. The product was treated with butyl isocyanate in a manner analogous to R06039-221 to afford (cis 3a,7a)-N-butyl-1-oxo-3,3-diphenylhexahydrofuro[3,4-c]pyridine-5(1H)-carboxamide. $^1$H NMR (300 MHz, CHLOROFORM-d) δ ppm 0.92 (t, J=7.35 Hz, 3H), 1.24-1.52 (m, 4H), 1.75-1.92 (m, 1H), 2.10 (d, J=13.94 Hz, 1H), 2.28 (dd, J=14.13, 11.87 Hz, 1H), 2.77-2.96 (m, 2H), 3.11-3.28 (m, 2H), 3.47-3.62 (m, 2H), 3.91 (dd, J=14.32, 5.65 Hz, 1H), 4.40 (t, J=5.27 Hz, 1H), 7.17-7.38 (m, 6H), 7.42-7.48 (m, 2H), 7.50-7.59 (m, 2H).

Example 53

R060039-212

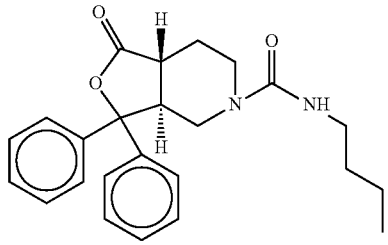

Chemical Formula: $C_{24}H_{40}N_2O_3$
Molecular Weight: 404.59

(trans 3a,7a)-N-Butyl-1-oxo-3,3-diphenylhexahydrofuro[3,4-c]pyridine-5(1H)-carboxamide. cis 1,1-Diphenyl-hexahydrofuro[3,4-c]pyridin-3-one (0.12 g, 0.41 mmol) was treated with NaH (60%, 0.04 g, 1.02 mmol) in THF and allowed to stir for 30 min at 0° C. The solution was diluted with H$_2$O (20 mL) and extracted with EtOAc (3×20 mL). The resulting organic layers were combined, dried (MgSO$_4$), and concentrated under reduced pressure to provide an oil as a mixture of cis and trans isomers. The mixture was treated with butyl isocyanate in a manner analogous to R06039-221. The resulting mixture of cis and trans isomers were purified on preparative HPLC to afford the pure trans isomer in 23% yield. $^1$H NMR (300 MHz, CHLOROFORM-d) δ ppm 0.94 (t, J=7.16 Hz, 3H), 1.30-1.71 (m, 6H), 2.10-2.43 (m, 2H), 2.59-2.90 (m, 2H), 3.16-3.38 (m, 2H), 3.74 (d, J=12.43 Hz, 1H), 4.49 (br. s., 1H), 4.96 (d, J=10.55 Hz, 1H), 7.12-7.22 (m, 2H), 7.28-7.44 (m, 6H), 7.51-7.59 (m, 2H).

Example 54

R06039-231

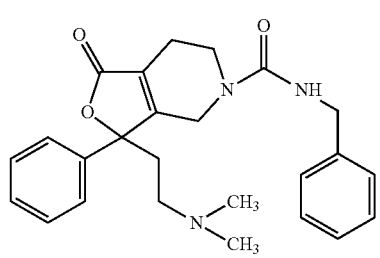

Chemical Formula: $C_{25}H_{29}N_3O_3$
Molecular Weight: 419.52

N-benzyl-3-(2-(dimethylamino)ethyl)-1-oxo-3-phenyl-3,4,6,7-tetrahydrofuro[3,4-c]pyridine-5(1H)-carboxamide. Benzyl isocyanate (0.017 g, 0.13 mmol) was added to a solution of 3-phenyl-3-(2-dimethylamino)ethyl-4,5,6,7-tetrahydrofuro[3,4-c]pyridin-1(3H)-one (0.037 g, 0.13 mmol prepared in a manner analogous to compound 2) in dichloromethane (10 mL) and was stirred at room temperature for 1 h. The solvent was removed and the resulting residue was purified on silica to give the desired product (0.015 g, 27%). $^1$H NMR (300 MHz, CHLOROFORM-d) δ ppm 2.15-2.19 (m, 6H), 2.20-2.53 (m, 6H), 3.23-3.38 (m, 1H), 3.59 (d, J=13.56 Hz, 1H), 3.86-3.98 (m, 1H), 4.38-4.44 (m, 2H), 4.49 (t, J=2.07 Hz, 1H), 4.98 (br. s., 1H), 7.20-7.44 (m, 10H).

Biological

In Vitro

Example 55

Binding Assays

Functional determinations: identification of functional antagonists at the NPS receptor utilized RD-HGA16 cells (Molecular Devices), a CHO cell line stably over-expressing the promiscuous Gq-protein Ga16. Two individual cell lines were created that stably express each NPS receptor variant (NPS Ile 260 107 and Asn107). Cells were loaded with the calcium sensitive dye calcium3 (Molecular Devices) for 1 h and compounds were assayed in separate experiments for intrinsic activity and for the ability to inhibit NPS activity as measured by calcium mobilization in the FlexStation assay. Test compound Ke values were determined by running an 8-point half-log NPS concentration response curve in the presence and absence of a single concentration of test compound. EC50 values were calculated for NPS (A) and NPS+ test compound (A0), and these used to calculate the test compound Ke. A three-parameter logistic equation was fit to the concentration response data with Prism (v5 for Windows, GraphPad Software; San Diego, Calif.) to calculate the EC50 values.

At least two different concentrations of test compound were used for these experiments, and these were chosen such that they at least caused a 4-fold rightward shift in the NPS EC50. The Ke was calculated from the formula: Ke=[L]/(DR−1), where [L] equals the concentration of test compound in the assay and DR equals the dose ratio (A0/A). The data represents mean±SE from at least three independent experiments.

In Vivo

Methods for inhibition of NPS induced locomotor stimulation: Male C57BL6 mice are used in all tests. Mice are injected i.c.v. with NPS (0.01, 0.1, 1 nmol) or saline as a control (total vol.: 2 μl). Simultaneously, an i.p. injection of antagonist is administered and locomotor activity monitored. The open field consists of four adjacent activity chambers (each 50×50×50 cm) monitored by an automated video motility system (PolyTrack, San Diego Instruments). Locomotor activity is recorded over 10 min. The imaginary central zone is defined as a 15×15 cm square in the middle of each observation area. Illumination in the central zone is 150 lux. Rearing, climbing, and horizontal activity is quantitated and evaluated for statistical significance.

Elevated Plus Maze.

The elevated plus maze consists of two open (30×5 cm) and two wall-enclosed arms (30×5×15 cm) connected by a central platform (5×5 cm). Light intensity on the open arms is 150 lux. The apparatus is elevated 75 cm above the floor. Behavioral testing is started by placing a mouse in the central area facing a closed arm in which the animal usually enters first.

Exploratory behavior is monitored by the same video motility system as for the open field over a period of 5 min. Numbers of entries into open arms, time and distance traveled in open and closed arms, general activity and latency until the first open-arm entry are recorded and quantified automatically. Entries are defined as the body center of an animal entering a new zone. Administration of test compound(s) is carried out as described for the open field test.

REFERENCES (1) Sato, S. S., Y.; Miyajima, N.; Yoshimura, K., 2002. Novel G-protein coupled receptor protein and DNA thereof. World Patent Application WO 02/31145 A1
(2) Xu, Y. L.; Reinscheid, R. K.; Huitron-Resendiz, S.; Clark, S. D.; Wang, Z.; Lin, S. H.; Brucher, F. A.; Zeng, J.; Ly, N. K.; Henriksen, S. J.; de Lecea, L.; Civelli, O. Neuropeptide S: a neuropeptide promoting arousal and anxiolytic-like effects. Neuron 2004, 43, 487-497.
(3) Rizzi, A.; Vergura, R.; Marzola, G.; Ruzza, C.; Guerrini, R.; Salvadori, S.; Regoli, D.; Calo, G. Neuropeptide S is a stimulatory anxiolytic agent: a behavioural study in mice. Br. J. Pharmacol. 2008.
(4) Reinscheid, R. K.; Xu, Y. L.; Okamura, N.; Zeng, J.; Chung, S.; Pai, R.; Wang, Z.; Civelli, O. Pharmacological characterization of human and murine neuropeptide s receptor variants. J Pharmacol Exp Ther 2005, 315, 1338-1345.
(5) Meis, S.; Bergado-Acosta, J. R.; Yanagawa, Y.; Obata, K.; Stork, O.; Munsch, T. Identification of a neuropeptide S responsive circuitry shaping amygdala activity via the endopiriform nucleus. PLoS ONE 2008, 3, e2695.
(6) Gottlieb, D. J.; O'Connor, G. T.; Wilk, J. B. Genome-wide association of sleep and circadian phenotypes. BMC Med Genet 2007, 8 Suppl 1, S9.

where the dotted lines denote a saturated or unsaturated bond, with the proviso that either all dotted lines denote an unsaturated bond, only the dotted line between e and f is an unsaturated bond or none of the dotted lines denote an unsaturated bond;

$X_1$ is either CH, $CH_2$, N or N—$R_3$ and $X_2$ is CH when $X_1$ is N, $X_2$ is $CH_2$ when $X_1$ is N—$R_3$, $X_2$ is N when $X_1$ is CH, and $X_2$ is N—$R_3$ when $X_1$ is $CH_2$;

m is 0 or 1;

the wavy lines represent bonds connected to carbons having cis- or trans-configuration;

$Y_1$ is O or S; $Y_2$ is O, N, or $CH_2$;

$R_1$ and $R_2$ are jointly structure (II):

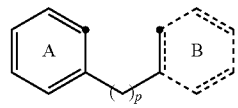

(II)

where p is 0 or 2 if ring B is present and p is 2 if ring B is not present; or $R_1$ and $R_2$ are each independently methyl alcohol, phenyl, straight chain or branched $C_{1-8}$ alkyl, $C_{3-6}$ cycloalkyl, $C_{2-8}$ alkenyl, $C_{2-8}$ alkynyl, $C_{6-10}$ aryl or heterocycle, substituted aryl, thiophene, furan, or one of the following structures:

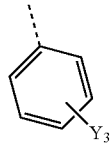

(1d)

where $Y_3$ may be at any position on the ring and is H, halogen, OH, $C_{1-4}$ alkyl, $C_{1-4}$ hydroxyalkyl, or $CF_3$;

What is claimed is:

1. A neuropeptide S receptor antagonist comprising a compound of structure (I):

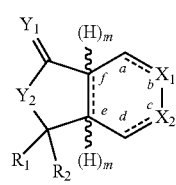

(I)

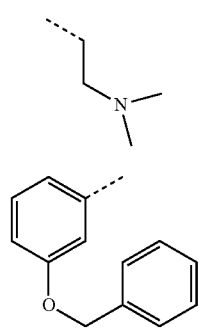

(1e)

(1f)

-continued (1g) [structure: ethyl acetate group]

(1h) [structure: naphthalenyl] or (1i) [structure: 2-(benzyloxy)phenyl];

and
R₃ is —C(=NH)NH₂, —CONH(CH₂)₃CH₃, —CONH(CH₂)₄CH₃,

[structure: tetrahydroisoquinoline carbonyl], [structure: thiocarbamoyl-ethyl-piperidine],

[structure: carbamoyl-ethyl-piperidine] or [structure: benzylcarbamoyl with R₆], where R₆ may be at any position on the ring and is H, NH₂, NHCOCH₃, —OCH₂CH₃, NHCO(CH₂)₄CH₃, N(CH₃)₂, NHCOOC(CH₃)₃, halogen, NHCOCH₂CH₂N—[cyclohexyl], —NHCO(CH₂)ₙ—[phenyl], wherein n is 0 to 3;

—NHCOCH=CH—[phenyl], —N[piperazine]N—CH₃,

—N[imidazole]N, NHCSNHCH₂CH₂—N[piperidine];

or R₃ is one of the following structures:

(3a) [2-nitrophenyl acetyl]

(3b) [2-nitrocinnamoyl]

(3c) [3-(2-aminophenyl)propanoyl]

(3d) [2-aminophenyl acetyl]

(3e) [2-naphthoyl]

(3f) [phenylpropynoyl]

(3g) [cinnamoyl]

(3h) [tetrahydroisoquinoline-3-carbonyl]

(3i) [tetrahydroisoquinoline-3-carbonyl, stereoisomer]

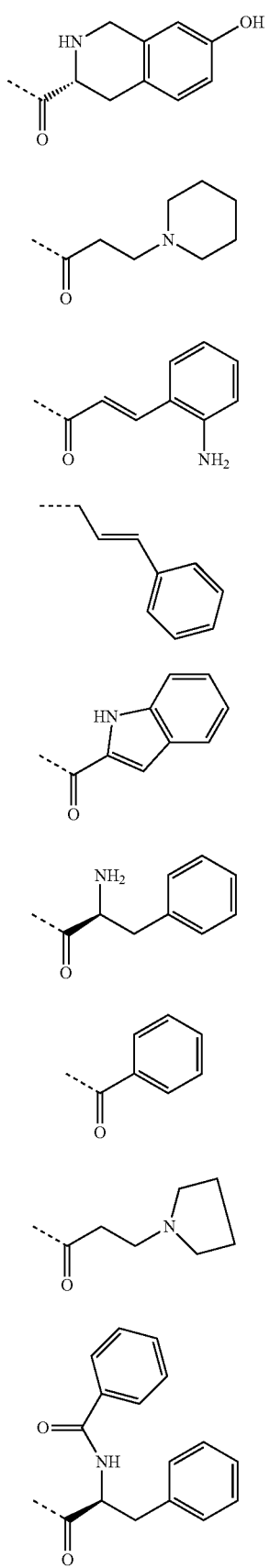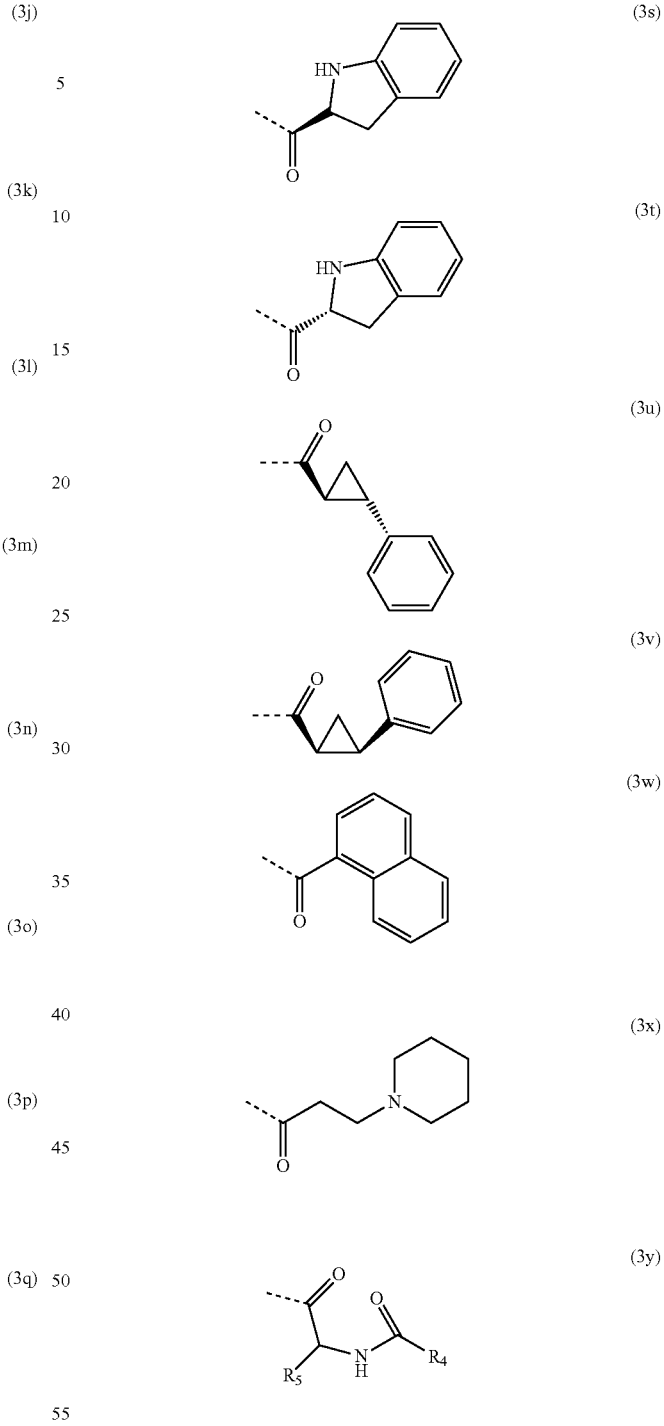

where $R_5$ is $C_{1-8}$ alkyl, $C_{3-6}$ cycloalkyl, $C_{2-8}$ alkenyl, $C_{2-8}$ alkynyl, $C_{6-10}$ aryl, heterocycle, substituted aryl, substituted thiophene, furan, pyrrole, a natural amino acid side chain, or an unnatural amino acid side chain selected from the group consisting of Norleucine, Cyclohexylalanine, Homocyclohexylalanine, Cyclohexylglycine, 2-amino isobutyric acid, 3-Cyclopentylalanine, Norvaline, and homophenylalanine; and $R_4$ is $C_{1-8}$ alkyl, $C_{3-6}$ cycloalkyl, $C_{2-8}$ alkenyl, $C_{2-8}$ alkynyl, $C_{6-10}$ aryl, heterocycle, substituted aryl, substituted thiophene, furan, pyrrole, or H; or (3z)

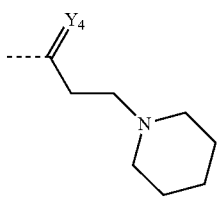

where Y$_4$ may be O or S.

2. A compound of claim 1 wherein R$_1$ is phenyl.

3. A compound of claim 1 wherein R$_2$ is isobutyl.

4. A compound of claim 1 wherein R$_1$ is phenyl and R$_2$ is isobutyl.

5. A compound of claim 1 wherein X$_2$ is N—R$_3$ and X$_1$ is CH$_2$.

6. The compound of claim 1, wherein R$_1$ and R$_2$ are each independently aryl having halogens at position 3 and 4 independently, aryl having alkoxy, methoxy, ethoxy, benzyloxy, hydroxyl at positions 2 and 3 independently, aryl having trifluoromethyl at position 4, or one of the following structures:

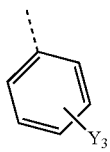

where Y$_3$ may be at any position on the ring and is H, halogen, OH, C$_{1-4}$ alkyl, C$_{1-4}$ hydroxyalkyl, or CF$_3$.

7. A compound of claim 1 having binding activity of Ke less than 200 nM.

8. A compound of claim 1 having binding activity of Ke less than 100 nM.

9. A pharmaceutically acceptable salt comprising a compound of claim 1.

10. A pharmaceutical composition comprising an effective amount of a neuropeptide-S-receptor antagonist compound of claim 1 and a physiologically acceptable carrier.

11. A method for treating at least one of a disease or condition attributable to binding of an agonist to the neuropeptide-S receptor in a mammal, which comprises administering an effective amount of a compound according to claim 1 or a salt thereof to said mammal wherein the disease or condition is selected from the group consisting of substance abuse, relapse from substance abuse, panic disorders, phobias, post-traumatic stress disorder, and sleep disorders.

12. The method of claim 11, wherein the sleep disorder is narcolepsy.

13. The method of claim 11, wherein the substance abuse is selected from the group consisting of opiate addiction, cocaine addiction, nicotine addiction and ethanol addiction.

14. The method of claim 11, wherein the compound is administered through an avenue selected from the group consisting of oral ingestion, injection, intravenous injection, tablet, capsule, syrup, aerosol, troche, bolus, suppository, ointment, powder, solution, dispersion, emulsion, and suspension.

15. The method of claim 11, wherein the mammal is a human.

* * * * *